US 8,190,251 B2

(12) United States Patent
Molnar et al.

(10) Patent No.: US 8,190,251 B2
(45) Date of Patent: May 29, 2012

(54) METHOD AND APPARATUS FOR THE TREATMENT OF MOVEMENT DISORDERS

(75) Inventors: Gregory F. Molnar, New Brighton, MN (US); Gabriela C. Miyazawa, Minneapolis, MN (US); Keith A. Miesel, Saint Paul, MN (US); Jonathan C. Werder, Corcoran, MN (US); David L. Carlson, Fridley, MN (US); Jonathon E. Giftakis, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1442 days.

(21) Appl. No.: 11/565,268

(22) Filed: Nov. 30, 2006

(65) Prior Publication Data
US 2007/0225674 A1    Sep. 27, 2007

Related U.S. Application Data

(60) Provisional application No. 60/785,506, filed on Mar. 24, 2006.

(51) Int. Cl.
*A61B 5/04* (2006.01)
(52) U.S. Cl. ........................................ 600/545; 600/544
(58) Field of Classification Search .......... 600/544–545; 607/2–3, 48, 68–69
See application file for complete search history.

(56) References Cited

U.S. PATENT DOCUMENTS

| 4,060,716 A | 11/1977 | Pekrul et al. |
| 4,557,270 A * | 12/1985 | John ............................. 600/544 |
| 4,663,703 A | 5/1987 | Axelby et al. |
| 4,791,548 A | 12/1988 | Yoshikawa et al. |
| 4,868,773 A | 9/1989 | Coyle et al. |
| 4,998,051 A | 3/1991 | Ito |
| 5,311,876 A | 5/1994 | Olsen et al. |
| 5,345,535 A | 9/1994 | Doddington |
| 5,347,446 A | 9/1994 | Iino et al. |
| 5,488,560 A | 1/1996 | Wood et al. |
| 5,509,927 A | 4/1996 | Epstein et al. |
| 5,519,605 A | 5/1996 | Cawlfield |
| 5,583,963 A | 12/1996 | Lozach |

(Continued)

FOREIGN PATENT DOCUMENTS
EP    0433626    6/1991
(Continued)

OTHER PUBLICATIONS

Notification of Transmittal of the International Search and the Written Opinion, dated Jul. 4, 2007 for corresponding PCT Application No. PCT/US2006/061609 (13 pgs.).

(Continued)

*Primary Examiner* — Patricia Mallari
*Assistant Examiner* — Michael D'Angelo
(74) *Attorney, Agent, or Firm* — Shumaker & Sieffert, P.A.

(57) ABSTRACT

A method, apparatus, and system for treating patients suffering from movement disorders having the ability to determine one or more biomarkers indicative of a disease state. In some embodiments, the biomarker may be used as a closed-loop feedback signal to control the delivery of therapy (such as electrical stimulation or drug therapy), and which may also be used as an indication of therapy effectiveness. One embodiment uses electrodes placed in the brain to measure EEG or local field potential (LFP) signals, from which the one or more biomarkers may be determined.

54 Claims, 10 Drawing Sheets

U.S. PATENT DOCUMENTS

| | | | |
|---|---|---|---|
| 5,694,342 | A | 12/1997 | Stein |
| 5,818,929 | A | 10/1998 | Yaguchi |
| 5,928,272 | A | 7/1999 | Adkins et al. |
| 5,995,868 | A * | 11/1999 | Dorfmeister et al. ......... 600/544 |
| 6,066,163 | A | 5/2000 | John |
| 6,081,144 | A | 6/2000 | Usuki et al. |
| 6,098,463 | A | 8/2000 | Goldberg |
| 6,121,817 | A | 9/2000 | Yang et al. |
| 6,134,474 | A | 10/2000 | Fischell et al. |
| 6,167,298 | A | 12/2000 | Levin |
| 6,227,203 | B1 | 5/2001 | Rise et al. |
| 6,341,236 | B1 | 1/2002 | Osorio et al. |
| 6,353,754 | B1 | 3/2002 | Fischell et al. |
| 6,442,506 | B1 | 8/2002 | Trevino |
| 6,473,639 | B1 | 10/2002 | Fischell et al. |
| 6,473,732 | B1 | 10/2002 | Chen |
| 6,480,743 | B1 | 11/2002 | Kirkpatrick et al. |
| 6,549,804 | B1 | 4/2003 | Osorio |
| 6,587,727 | B2 | 7/2003 | Osorio et al. |
| 6,658,287 | B1 | 12/2003 | Litt et al. |
| 6,671,555 | B2 | 12/2003 | Gielen et al. |
| 6,745,076 | B2 | 6/2004 | Wohlgemuth et al. |
| 6,768,969 | B1 | 7/2004 | Nikitin et al. |
| 6,904,390 | B2 | 6/2005 | Nikitin et al. |
| 6,920,357 | B2 | 7/2005 | Osorio et al. |
| 7,146,211 | B2 | 12/2006 | Frei et al. |
| 7,146,218 | B2 | 12/2006 | Esteller et al. |
| 7,174,206 | B2 | 2/2007 | Frei et al. |
| 7,177,674 | B2 | 2/2007 | Echauz et al. |
| 7,242,983 | B2 | 7/2007 | Frei et al. |
| 2002/0103512 | A1 | 8/2002 | Echauz et al. |
| 2002/0169485 | A1 | 11/2002 | Pless et al. |
| 2003/0004428 | A1 | 1/2003 | Pless et al. |
| 2003/0073917 | A1 | 4/2003 | Echauz et al. |
| 2003/0149456 | A1 | 8/2003 | Rottenberg et al. |
| 2003/0149457 | A1 * | 8/2003 | Tcheng et al. .................. 607/48 |
| 2003/0187621 | A1 | 10/2003 | Nikitin et al. |
| 2003/0195574 | A1 | 10/2003 | Osorio et al. |
| 2004/0006264 | A1 | 1/2004 | Mojarradi et al. |
| 2004/0133119 | A1 | 7/2004 | Osorio et al. |
| 2004/0133120 | A1 | 7/2004 | Frei et al. |
| 2004/0133248 | A1 | 7/2004 | Frei et al. |
| 2004/0133390 | A1 | 7/2004 | Osorio et al. |
| 2004/0136453 | A1 | 7/2004 | Lin et al. |
| 2004/0138516 | A1 | 7/2004 | Osorio et al. |
| 2004/0138517 | A1 | 7/2004 | Osorio et al. |
| 2004/0138518 | A1 | 7/2004 | Rise et al. |
| 2004/0138536 | A1 | 7/2004 | Frei et al. |
| 2004/0138581 | A1 | 7/2004 | Frei et al. |
| 2004/0138647 | A1 | 7/2004 | Osorio et al. |
| 2004/0138711 | A1 | 7/2004 | Osorio et al. |
| 2004/0152958 | A1 | 8/2004 | Frei et al. |
| 2004/0158119 | A1 | 8/2004 | Osorio et al. |
| 2004/0181263 | A1 | 9/2004 | Balzer et al. |
| 2005/0010265 | A1 | 1/2005 | Baru Fassio et al. |
| 2005/0021313 | A1 | 1/2005 | Nikitin et al. |
| 2005/0081847 | A1 | 4/2005 | Lee et al. |
| 2005/0197590 | A1 | 9/2005 | Osorio et al. |
| 2006/0015034 | A1 * | 1/2006 | Martinerie et al. ........... 600/544 |
| 2006/0058856 | A1 | 3/2006 | Morell |
| 2006/0094973 | A1 | 5/2006 | Drew |
| 2006/0135877 | A1 | 6/2006 | Giftakis et al. |
| 2006/0135881 | A1 | 6/2006 | Giftakis et al. |
| 2006/0136006 | A1 | 6/2006 | Giftakis et al. |
| 2006/0195144 | A1 | 8/2006 | Giftakis et al. |
| 2006/0224067 | A1 | 10/2006 | Giftakis et al. |

FOREIGN PATENT DOCUMENTS

| | | |
|---|---|---|
| EP | 1500409 | 1/2005 |
| WO | 9515117 | 6/1995 |
| WO | 9726823 | 7/1997 |
| WO | 0175660 | 10/2001 |
| WO | 02089913 | 11/2002 |
| WO | 2004034883 | 4/2004 |
| WO | 2004034982 | 4/2004 |
| WO | 2004043536 | 5/2004 |
| WO | 2005061045 | 7/2005 |

OTHER PUBLICATIONS

Response to Written Opinion, dated Oct. 3, 2007 for corresponding PCT Application No. PCT/US2006/061609 (3 pgs.).

A New Algorithm for Order Statistic and Sorting, Barun K. Kar and Dhiraj K. Pradhan, IEEE Transactions on Signal Processing, vol. 41, No. 8, Aug. 1993, pp. 2688-2694.

Frei, Mark G., Parametric Identification in Continuous-Time Stochastic Systems Using Time and Space Weighted Least Squares, Dissertation, Dec. 7, 1993, submitted to the University of Kansas Department of Mathematics.

Nikitin, Alexei V., Pulse Pileup Effects in Counting Detectors, Dissertation, submitted to the University of Kansas Department of Physics and Astronomy, published Aug. 29, 1999.

Nikitin, Alexei V. et al., Many-fold Coincidence Pileup in Silicon Detectors: Solar X-Ray Response of Charged Particle Detector System for Space, Elsevier Science, Aug. 16, 1996.

Nikitin, Alexei V., et al., The effect of pulse pile-up on threshold crossing rates in a system with a known impulse response, Elsevier Science, Nov. 15, 1997.

Harrison MAF, Frei MG, Asuri S, Osorio, I, Lai Y-C. Correlation dimension and integral do not predict epileptic seizures. Chaos. Jul. 26, 2005;15, 033106. doi:10.1063/1.1935138.

Harrison MAF, Frei MG, Osorio I. Accumulated energy revisited. Clin Neurophysiol. Mar. 2005;116(3):527-31. doi:10.1016/j.clinph. 2004.08.022.

Lai Y-C, Harrison MAF, Frei MG, Osorio I. Reply to Comment on Inability of Lyapunov exponents to predict epileptic seizures.Physical Review Letters. 2005;94;019802.

Osorio I, Frei MG, Sunderam S, Giftakis J, Bhavaraju NC, Schaffner SF, Wilkinson SB. Automated seizure abatement in humans using electrical stimulation. Ann Neur. Jan. 24, 2005;57(2):258-68.

Sunderam S, Frei MG, Osorio I. Predictability of the interseizure interval demonstrated by using a discrete sequence of automated detection times. Abstract; Epilepsia. 2004;45(S7):284.

Bhavaraju NC, Frei MG, Osorio I. Real-time automated seizure detection and quantitative analysis in analog: method and performance evaluation. Abstract; Epilepsia. 2004;45(S7):327.

Osorio I, Frei MG, Sunderam S, Giftakis J, Bhavaraju NC, Schaffner SF, Wilkinson SB. Automated seizure abatement in humans using electrical stimulation. Abstract; Epilepsia. 2004;45(S7):330.

Graves NM, Lozano AM, Wennberg RA, Osorio I, Wilkinson S, Baluch G, French JA, Kerrigan JF Shetter A, Fisher RA. Brain stimulation for epilepsy: Pilot patient results and implementation of a controlled clinical trial. Abstract; Epilepsia 2004;45(S7):148.

Lai Y-C, Harrison MAH, Frei MG, Osorio I. Controlled test for predictive power of Lyapunov exponents: Their inability to predict epileptic seizures. Chaos. Sep. 2004;14(3):630-42.

Meng L, Frei MG, Osorio I, Strang G, Nguyen TQ. Gaussian mixture models of EcoG signal features for improved detection of epileptic seizure. Medical Engineering and Physics. 2004;26(5):379-93.

Harrison MAF, Osorio I, Frei MG, Lai Y-C, Asuri S. Seizure prediction and detection with correlation integrals. Abstract; Epilepsia. 2003; 44(S9):229. Proceedings of the American Epilepsy Society Meeting, Boston, MA. Dec. 5-10, 2003.

Lai Y-C, Harrison MAF, Frei MG, Osorio I. Inability of Lyapunov exponents to predict epileptic seizures. Phys Rev Lett. Aug. 8, 2003;91(6):068102.

Hass SH, Frei MG, Osorio I, Pasik-Duncan B, Radel J. EEG ocular artifact removal through ARMAX model system identification using extended least squares. Comm Info Systems. Jun. 2003;3(1):19-40.

Sunderam S and Osorio I. Mesial temporal lobe seizures may activate thermoregulatory mechanisms in Humans: An infrared study of facial temperature. Epilepsy and Behavior. Aug. 2003;4(4):399-406.

Osorio I, Frei MG, Giftakis J, Peters T, Ingram J, Turnbull M, Herzog M, Rise M, Schaffner S, Wennberg R, Walczak T,.Risinger M, Ajomone-Marsan C. Performance re-assessment of a real-time seizure detection algorithm on long ECoG series. Epilepsia. Dec. 2002;43(12):1522-35.

Bhavaraju NC, Nagaraddi V, Chetlapalli SR, and Osorio I. Electrical and thermal behavior of non-ferrous noble metal electrodes exposed to MRI fields. Magnetic Resonance Imaging. May 2002;20(4):351-57.

Lai Y-C, Osorio I, Harrison MAF, Frei, MG. Correlation-dimension and autocorrelation fluctuations in seizure dynamics. Physical Review E Stat Nonlin Soft Matter Phys. Mar. 2002;65(3 Pt 1):031921.

Peters TE, Bhavaraju NC, Frei MG, Osorio I. Network system for automated seizure detection and contingent delivery of therapy. J Clin Neurophysiol. Nov. 2001;18(6):545-9.

Sunderam S, Osorio I, Watkins III JF, Wilkinson SB, Frei MG, and Davis RE. Vagal and sciatic nerve stimulation have complex time-dependent effects on chemically induced seizures: A controlled study. Brain Res. Nov. 2001;9;918 (1-2):60-6.

Osorio I, Frei MG, Manly BFJ, Sunderam S, Bhavaraju NC, and Wilkinson SB. An introduction to contingent (closed-loop) brain electrical stimulation for seizure blockage, to ultra-short term t and to multidimensional statistical analysis of therapeutic efficacy. J Clin Neurophysiol. Nov. 2001;18(6):533-44.

Johnson AM, Frei MG, Sunderam S, Asuri S, Osorio I. Application of the intrinsic timescale decomposition (ITD) algorithm to EEG seizure detection. Abstract; Epilepsia. 42(S7);37. Proceeding of the American Epilepsy Society, American Clinical Neurophysiology Society Annual Meeting, Philadelphia, PA, Nov. 30-Dec. 5, 2001.

Ingram JL, Osorio I, Wilinson SB. Anterior thalamic neclei evoked responses: A preliminary study. Abstract; Epilepsia.42(S7);29. Proceeding of the American Epilepsy Society, American Clinical Neurophysiology Society Annual Meeting, Philadelphia, PA, Nov. 30-Dec. 5, 2001.

Peters T, Frei MG, Bhavaraju NC, Sunderam S, Osorio I. Network system for bedside automated seizure detection and stimulation. Abstract; Epilepsia. 42(S7);40. Proceeding of the American Epilepsy Society, American Clinical Neurophysiology Society Annual Meeting, Philadelphia, PA, Nov. 30-Dec. 5, 2001.

Osorio I, Frei MG, Wilkinson SB, Sunderam S, Bhavaraju NC, Graves N, Schaffner SF, Peters T, Johnson AM, DiTeres, CA, Ingram J, Nagaraddi V, Overman J, Kavalir MA, Turnbull M. Seizure blockage with automated "closed-loop" electrical stimulation: A pilot study. Abstract; Epilepsia. 42(S7);207. Proceeding of the American Epilepsy Society, American Clinical Neurophysiology Society Annual Meeting, Philadelphia, PA, Nov. 30-Dec. 5, 2001.

Frei MG, Osorio I, Giftakis JE, Herzog MH, Rise MT, Schaffne, SF, Johnson AM, DiTeresi CA, Peters T, Ingram J, Ajmone-Marsan C. Performance assessment of FHS seizure detection algorithm on Long ECoG Series. Abstract; Epilepsia. 42(S7);37. Proceeding of the American Epilepsy Society, American Clinical Neurophysiology Society Annual Meeting, Philadelphia, PA, Nov. 30-Dec. 5, 2001.

Bhavaraju NC, Nagaraddi V, Osorio I. Electrical and thermal behavior of intracranial electrodes during magnetic resonance imaging: A quantitative study. Abstract; Epilepsia. 42(S7);62. Proceeding of the American Epilepsy Society, American Clinical Neurophysiology Society Annual Meeting, Philadelphia, PA, Nov. 30-Dec. 5, 2001.

Thompson MM, Dubin JE, Eckard D, Troster AI, Osorio I. The WADA test has nonselective effects in the brain: A power spectral stydy. Abstract; Epilepsia. 42(S7);243. Proceeding of the American Epilepsy Society, American Clinical Neurophysiology Society Annual Meeting, Philadelphia, PA, Nov. 30-Dec. 5, 2001.

Brown, "Oscillatory nature of Human Basal Ganglia Activity: Relationship to the Pathophysiology of Parkinson's Disease", Movement Disorders vol. 18, No. 4, 2003, pp. 357-363.

Brown et al., "Dopamine Dependency of Oscillations between Subthalamic Nucleus and Pallidum in Parkinson's Disease", J. of Neuroscience, Feb. 1, 2001, 21(3), pp. 1033-1038.

Brown et al., "Effects of stimulation of the subthalamic area on oscillatory pallidal activity in Parkinson's disease", Experimental Neurology 188 (2004), pp. 480-490.

Brown et al., "Basal ganglia local field potential activity: Character and functional significance in the human", Clinical Neurophysiology 116 (2005), pp. 2510-2519.

Chen et al., "Oscillatory pallidal local field potential activity correlates with involuntary EMG in dystonia", Neurology, 2006, 66, pp. 418-420.

Foffani et al., "300-Hz subthalamic oscillations in Parkinson's disease", Brain (2003), 126, pp. 2153-2163.

Foffani et al., "Subthalamic oscillatory activities at beta or higher frequency do not change after high-frequency DBS in Parkinson's disease", Brain Research Bulletin 69 (2006), pp. 123-130.

Hutchison et al., "Neuronal Oscillations in the Basal Ganglia and Movement Disorders: Evidence from Whole Animal and Human Recordings", J. of Neuroscience, (Oct. 20, 2004), 24(42), pp. 9240-9243.

Kühn et al., "Event-related beta desynchronization in human subthalamic nucleus correlates with motor performance", Brain (2004), 127, pp. 735-746.

Levy et al., "High-frequency Synchronization of Neuronal Activity in the Subthalamic Nucleus of Parkinsonian Patients with Limb Tremor", J. of Neuroscience, (Oct. 15, 2000), 20(20), pp. 7766-7775.

Levy et al., "Synchronized Neuronal Discharge in the Basal Ganglia of Parkinsonian Patients is Limited to Oscillatory Activity", J. of Neuroscience, (Apr. 1, 2002), 22(7), pp. 2855-2861.

Silberstein et al., "Patterning of *globus pallidus* local field potentials differs between Parkinson's disease and dystonia", Brain (2003), 126, pp. 2597-2608.

Trottenberg et al., "Subthalamic gamma activity in patients with Parkinson's disease", Experimental Neurology (2006), pp. 1-10.

Wingeier et al., "Intra-operative STN DBS attenuates the prominent beta rhythm in the STN in Parkinson's disease", Experimental Neurology 197 (2006), pp. 244-251.

Nini et al., "Neurons in the Globus Pallidus Do Not Show Correlated Activity in the Normal Monkey, but Phase-Locked Oscillations Appear in the MPTP Model of Parkinsonism", J. of Neurophysiology, vol. 74, No. 4, Oct. 1995, pp. 1800-1805.

X. Liu et al., "The oscillatory activity in the Parkinsonian subthalamic nucleus investigated using the macro-electrodes for deep brain stimulation", Clinical Neurophysiology 113 (2002) pp. 1667-1672.

Dostrovsky et al., "Oscillatory activity in the basal ganglia—relationship to normal physiology and pathophysiology", Brain (2004) vol. 127 No. 4, pp. 721-722.

Gatev et al., "Oscillations in the Basal Ganglia Under Normal Conditions and in Movement Disorders", Movement Disorders vol. 21, No. 10, 2006, pp. 1566-1577.

Frei MG, Osorio I. Left vagus nerve stimulation with the neurocybernetic prosthesis has complex effects on heart rate and on its variability in humans. Epilepsia. Aug. 2001;42(8):1007-1016. Presented in part at the American Epilepsy Society Annual Meetings San Francisco, CA, 1996, and San Diego, CA, 1998.

Sunderam S, Osorio I, Frei MG, Watkins III JF. Stochastic modeling and prediction of experimental seizures in sprague-dawley rats. J Clin Neurophysiol. May 2001;18(3):275-282.

Osorio I, Harrison MAF, Frei MG, Lai YC. Observations on the application of the correlation dimension and correlation integral to the prediction of seizures. J Clin Neurophysiol. May 2001;18(3);269-274.

Ingram J, Sunderam S, Frei MG, Osorio, I. Autonomic regulation during complex partial seizures: A thermographic study. Abstract; Epilepsia. 41(S7);59. Proceedings of the 54th Annual Meeting of the American Epilepsy Society, Los Angeles, CA, Dec. 1-6, 2000.

Sunderam S, Watkins III JF, Frei MG, and Osorio I. A stochastic analysis of ictal-interictal transitions during experimental seizures: Seizure duration depends on the duration of preceding ictal and interictal states. Abstract; Epilepsia. 41(S7);49. Proceedings of the 54th Annual Meeting of the American Epilepsy Society, Los Angeles, CA, Dec. 1-6, 2000.

DiTeresi CA, Thompson M, Frei MG, Sunderam S, and Osorio I. Loss of function during partial seizures: A quantitative study in humans. Abstract; Epilepsia. 41(S7);237. Proceedings of the 54th Annual Meeting of the American Epilepsy Society, Los Angeles, CA, Dec. 1-6, 2000.

Nagaraddi V, Wilkinson SB, Osorio I. The effect of one hertz stimulation on kindled seizures in rats. Abstract; Proceeding of the 54th Annual Meeting of the American Epilepsy Society, Los Angeles, CA, Dec. 1-6, 2000.

Frei MG, Davidchack R, Osorio I. Least squares acceleration filtering for estimating signal derivatives and Sharpness at extrema. IEEE. Aug. 1999; 46(8):971-977.

Osorio I, Frei MG, Wilkinson SB. Real time automated detection and quantitative analysis of seizures and short term predictions of clinical onset. Epilepsia. 1998;39(S16):615-627.

Thomas CV, Angel CA, Watkins JM, Frei MG, Bunag RD, Osorio I. Effects of vagal and sciatic stimulation on 3-MPA-induced seizures in rats. Epilepsia. 1998;39(S6):29.

Frei MG, Haas SM, Ingram JL, Osorio I. Filter design methods for improved seizure detection. Epilepsia. 1998;39 (S6):108.

Powell J, Frei MG, Davidchak R, Watkins JM, Wilkinson SB, Osorio I. Ictal tachycardia does not closely correlate with electrographic onset of ictal ECoG frequency changes. Epilepsia. 1998;39(S6):112.

Frei MG, Davidchack R, Osorio I. Effects of vagal stimulation on human ECG. Epilepsia. 1998:39(S6):200.

Frei MG, Osorio I, Davidchack R. A reappraisal of the value of EKG in the detection of epileptic seizures. Abstract;.Epilepsia. 1996:37(S5). Poster presentation, 50th Annual Meeting of the American Epilepsy Society, San Francisco, CA., Dec. 8, 1996.

Han P, Frei MG, Osorio I. Probable mechanisms of action of vagus nerve stimulation in humans with epilepsy: Is the heart a window into the brain? Abstract; Epilepsia. 1996:37(S5):83. Platform presentation, 50th Annual Meeting of the American Epilepsy Society, San Francisco, CA, Dec. 8, 1996.

Frei MG, Osorio I, Wilkinson SB. Quantitative analysis of inter-ictal vs. ictal ECoG signals. Abstract; Epilepsia. 1995:36 (S4):5. Poster presentation, 49th Annual Meeting of the American Epilepsy Society, Baltimore, MD, Dec. 4, 1995.

Osorio I, Frei MG, Lerner D, Wilkinson S. A method for accurate automated real time seizure detection. Abstract;.Epilepsia. 1995:36(S4):4. Poster presentation, 49th Annual Meeting of the American Epilepsy Society, Baltimore, MD, Dec. 4, 1995.

Ingram J, Osorio I, Frei MG, Wilkinson SB, Troster A. Temporo—spatial behavior of seizures of temporal lobe origin. Abstract; Epilepsia. 1995:36(S4):9. Poster presentation, 49th Annual Meeting of the American Epilepsy Society, Baltimore, MD, Dec. 4, 1995.

Hayden R, Lerner D, Osorio I, Lai YC, Frei MG.Correlation dimension does not distinguish ictal from interictal activity or noise. Abstract; Epilepsia. 1995:36(S4):5. Poster presentation, 49th Annual Meeting of the American Epilepsy Society, Baltimore, MD, Dec. 4, 1995.

Osorio I, Frei MG, Lerner D, Wilkinson SB. Automated rapid seizure detection in the human ECoG. Abstract in Proceedings of the IEEE Computer-Based Medical Systems, Lubbock, TX, Jun. 9-12, 1995.

Blum M, Floyd R, Vaughan P, Rivest R, Tarjan R. Linear Time Bounds for Median Computations. Abstract in *, Aug. 1971.

Hastad J. Median finding. Advanced Algorithms. Lecture 11: May 3, 1995.

Leutmezer et al., "Electrocardiographic Changes at Seizure Onset," Epilepsia, 2003, pp. 348-354, 44(3).

Rocamora et al., "Cardiac Asystole in Epilepsy: Clinical and Neurophysiologic Features," Epilepsia, 2003, pp. 179-185, 44(2).

Tavernor et al., "Electrocardiograph QT Lengthening Associated with Epileptiform EEG Discharges—A Role in Sudden Unexplained Death in Epilepsy," Seizure, Mar. 1996, pp. 79-83, 5(1).

Devinsky, "Effects of Seizures on Autonomic and Cardiovascular Function," Epilepsy Currents, Mar./Apr. 2004, pp. 43-46, 4(2).

Donner et al., "Sudden Unexplained Death in Children with Epilepsy," Neurology, 2001, pp. 430-434, 57.

Nei, et al., "EEG and ECG in Sudden Unexplained Death in Epilepsy," Epilepsia, 2004, pp. 338-345, 45(4).

Sorting Continuous—Time Signals and the Analog Median Filter, Paulo J. S. G. Ferreira, IEEE Signal Processing Letters, vol. 7, No. 10, Oct. 2000, pp. 281-283.

A Review of Median Filter Systems for Analog Signal Processing, Tiina Jarske and Olli Vainio, Analog Integrated Circuits and Signal Processing 3, pp. 127-135.

Median Filtering by Threshold Decomposition, J. Patrick Fitch, Edward J. Coyle, and Neal C. Gallagher, Jr., IEEE Transactions on Acoustics, Speech, and Signal Processing, vol. ASSP-32, No. 6, Dec. 1984, pp. 1183-1188.

Design and Implementation of a Single-Chip 1-D Median Filter, Kemal Oflazer, IEEE Transactions on Acoustics, Speech and Signal Processing, vol. ASSP-31, No. 5, Oct. 1983, pp. 1164-1168.

Direct Analog Rank Filtering, Kiichi Urahama and Takeshi Nagao, IEEE Transactions on Circuits and Systems-I: Fundamental Theory and Applications, vol. 42, No. 7, Jul. 1995, pp. 385-388.

Harrison MAF, Osorio I, Lai YC, Frei MG. Correlation dimension and correlation integral are sensitive to ECoG amplitude and power spectral density variation. Abstract; Epilepsia. 42(S7);37. Proceeding of the American Epilepsy Society, American Clinical Neurophysiology Society Annual Meeting, Philadelphia, PA, Nov. 30-Dec. 5, 2001.

Design of a Switched-Current Median Filter, C. K. Tse and K. C. Chun, IEEE Transactions on Circuits and Systems-II: Analog and Digital Signal Processing, vol. 42, No. 5, May 1995, pp. 356-359.

OSNet: A Neural Network Implementation of Order Statistic Filters, Pingnan Shi and Rabab K. Ward, IEEE Transactions on Neural Networks, vol. 4, No. 2, Mar. 1993, pp. 234-241.

Abstract of Analog Implementation of Seizure Detection Algorithm, Nikitin et. al., BMES/EMBS Conference, 1999. Proceedings of the First Joint, Oct. 13-16, 1999, pp. 860 vol. 2.

Analog Implementation of Seizure Detection Algorithm, Nikitin et. al., Flint Hills Scientific LLC.

High Speed FPGA Implementation of Median Filters, Bela Feher and Gabor Szedo, NDES '98 Nonlinear Dynamics of Electronic Systems, Tech. University of Budapest, Hungary Jul. 16-18, 1998, pp. 191-119.

Deterministic Properties of Analog Median Filters, Murk J. Bottema, IEEE Transactions on Information Theory, vol. 37, No. 6, Nov. 1991, pp. 1629-1640.

Analysis of the Properties of Median and Weighted Median Filters Using Threshold Logic and Stack Filter Representation, Olli Yli-Harja, Jaakko Astola and Yrjo Neuvo, IEEE Transactions on Signal Processing, vol. 39, No. 2, Feb. 1991, pp. 395-410.

Properties of Analog Median Filters, Steffan Paul, Knut Huper adn Josef A. Nossek, Non-Linear Digital Signal Processing 1993, IEEE Writer Workshop Jan. 17-20, 1993.

Stack Filters, Peter D. Wendt, Edward J. Coyle, adn Neal C. Gallagher, IEEE Transactions on Acoustics, Speech and Signal Processing, vol. ASSP-34, No. 4, Aug. 1986, pp. 898-911.

Output Distributions of Recursive Stack Filters, Ilya Shmulevich, Olli Yli-Harja, Karen Egiazarian, and Jaakko Astola, IEEE Signal Processing Letters, vol. 6, No. 7, Jul. 1999, pp. 175-178.

Binary Partition Algorithms and VLSI Architectures for Median and Rank Order Filtering, Charng Long Lee and Chein-Wei Jen, IEEE Transactions on Signal Processing, vol. 41, No. 9, Sep. 1993, pp. 2937-2942.

* cited by examiner

METHOD AND APPARATUS FOR THE TREATMENT OF MOVEMENT DISORDERS

FIELD OF THE INVENTION

The present invention relates generally to implantable medical devices (IMDs), and more particularly relates to systems and methods for treating movement disorders in a patient with an IMD.

BACKGROUND OF THE INVENTION

Nervous system disorders affect millions of people, causing a degradation of life, and in some cases, death. Nervous system disorders may include disorders of the central nervous system and peripheral nervous system. Some nervous system disorders may be considered "neurological movement disorders," and may include, for example without limitation, epilepsy, Parkinson's disease, essential tremor, dystonia, and multiple sclerosis (MS). Additionally, neurological movement disorders may include mental health disorders and psychiatric disorders which also affect millions of individuals and include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (e.g., narcolepsy), obesity, anorexia, and chronic pain disorders. Neurological movement disorders may be characterized by periods of involuntary movements and/or loss of muscle control.

As an example of a neurological movement disorder, Parkinson's Disease (PD) is generally characterized by poverty and slowness of movement (akinesia and bradykinesia), muscle stiffness (rigidity), tremor at rest, and gait and balance abnormalities that may lead to an inability to perform normal daily life activities. Some patients suffering from neurological movement disorders may also develop symptoms called dyskinesias and motor fluctuations, which may be a side effect of certain anti-Parkinson's medication. It is believed that PD is caused by the degeneration of dopaminergic neurons in the substantia nigra pars compacta, a brain structure of the basal ganglia involved in the control of movement. The loss of dopamine in the basal ganglia is believed to secondarily cause a cascade of abnormal activity in the other nuclei of the basal ganglia, thalamus and cortex. This has been detected in animals and humans as changes in neuronal firing patterns, firing frequencies, and in the tendency of these neurons to fire in an oscillatory manner. These abnormal oscillations and firing patterns are thought to underlie the classic motor symptoms of PD and have been shown to be reversible with the dopamine medication used to effectively treat PD.

There are various approaches in treating nervous system disorders, such as neurological movement disorders. Treatment therapies can include any number of possible modalities alone or in combination including, for example, electrical stimulation, magnetic stimulation, drug infusion, and/or brain temperature control. Each of these treatment modalities may be employed using closed-loop feedback control. Such closed-loop feedback control techniques may receive neurological signals (e.g., from a monitoring element) carrying information about a symptom or a condition of a nervous system disorder. Such a neurological signal can include, for example, electrical signals (such as local field potentials (LFPs), electroencephalogram (EEG), electrocorticogram (ECoG), and/or electrocardiogram (EKG) signals), chemical signals, and/or other types of biological signals (such as changes in the quantity of neurotransmitters).

For example, U.S. Pat. No. 5,995,868 to Dorfmeister et al., incorporated herein by reference in relevant part, discloses a system for the prediction, rapid detection, warning, prevention, or control of changes in activity states in the brain of a patient. Use of such a closed-loop feed back system for treatment of a nervous system disorder may provide significant advantages.

BRIEF SUMMARY OF THE INVENTION

In embodiments of the invention, a method, device, or system for assessing a neurological movement disorder includes the measurement and use of a biomarker that is a function of measured oscillatory activity in one or more frequency ranges.

In various embodiments of the invention, methods, devices, and systems for delivering therapy to treat a neurological movement disorder include the measurement and use of a biomarker to provide closed-loop feedback control to such therapy.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

Figure 1:
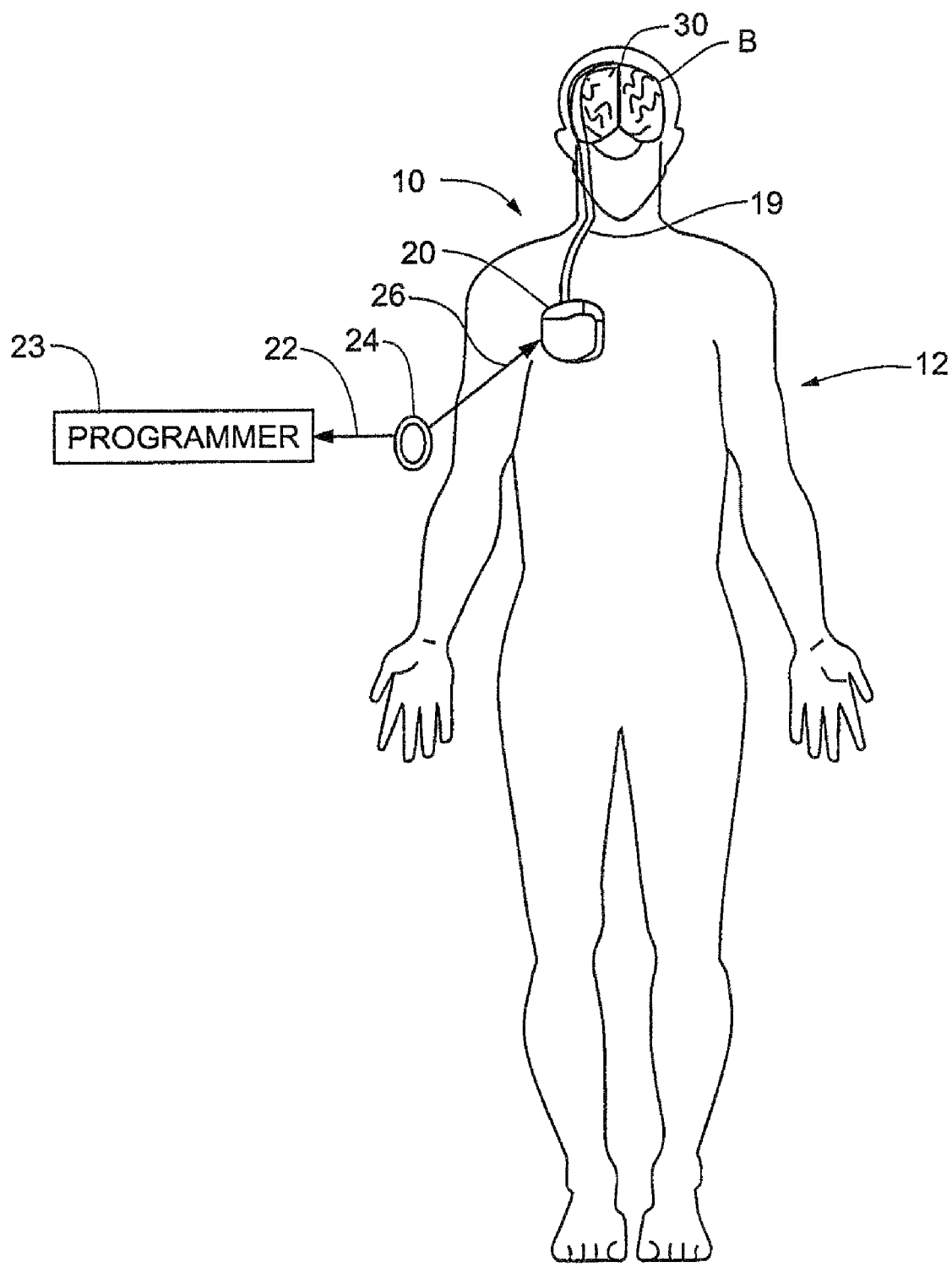
FIG. 1 shows an implantable system for treating a nervous system disorder according to an embodiment of the invention.

The following discussion is presented to enable a person skilled in the art to make and use the invention. Various modifications to the illustrated embodiments will be readily apparent to those skilled in the art, and the principles herein may be applied to other embodiments and applications without departing from the scope of the embodiments of the invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the invention as claimed.

FIG. 1 shows an embodiment of an implanted system 10 for treatment of a nervous system disorder, such as a neurological movement disorder, in accordance with an embodiment of the invention. System 10 includes IMD 20, lead(s) 19, and electrode(s) 30. Although the implanted system 10 is discussed herein in the context of monitoring and recording brain activity and/or providing brain stimulation, it will be appreciated that the implanted system 10 may also be used to monitor and record physiological signals from, or provide treatment therapies to, other locations of the body. The IMD 20 could, for example, be a neurostimulator device, a pacing device, a defibrillation device, an implantable loop recorder, a hemodynamic monitor that does not provide a pacing therapy, or any other implantable signal recording device known in the art or developed in the future. In FIG. 1, the IMD 20 is electrically coupled to the brain B of patient 12 through electrodes 30 and lead conductor(s) of at least one lead 19 in a manner known in the art. The electrodes 30 may also serve as therapy delivery elements to treat nervous system disorders. The IMD 20 may continuously or intermittently communicate with an external programmer 23 (e.g., patient or physician programmer) via telemetry using, for example, antenna 24 to relay radio-frequency signals 22, 26 between IMD 20 and programmer 23. In this embodiment, each of the features and functionalities discussed herein are provided by the IMD 20.

Those skilled in the art will appreciate that some medical device systems may take any number of forms from being fully implanted to being mostly external and can provide treatment therapy to any number of locations in the body. For example, the medical device systems described herein may be utilized to provide vagal nerve stimulation, for example, as disclosed in U.S. Pat. No. 6,341,236 (Osorio, et al.), incorporated by reference in relevant part. In addition, the treatment therapy being provided by the medical device systems may vary and can include, for example, electrical stimulation, magnetic stimulation, drug infusion, and/or brain temperature control (e.g., cooling). Moreover, it will be appreciated that the medical device systems may be utilized to analyze and treat any number of nervous system disorders. In the event that closed-loop feedback control is provided, the medical device system can be configured to receive any number of physiological signals that carry information about a symptom or a condition of a nervous system disorder. Such signals may be provided using one or more monitoring elements such as monitoring electrodes or sensors. For example, U.S. Pat. No. 6,227,203 provides examples of various types of sensors that may be used to detect a symptom or a condition or a nervous system disorder and responsively generate a neurological signal and is hereby incorporated by reference in relevant part.

Figure 2:
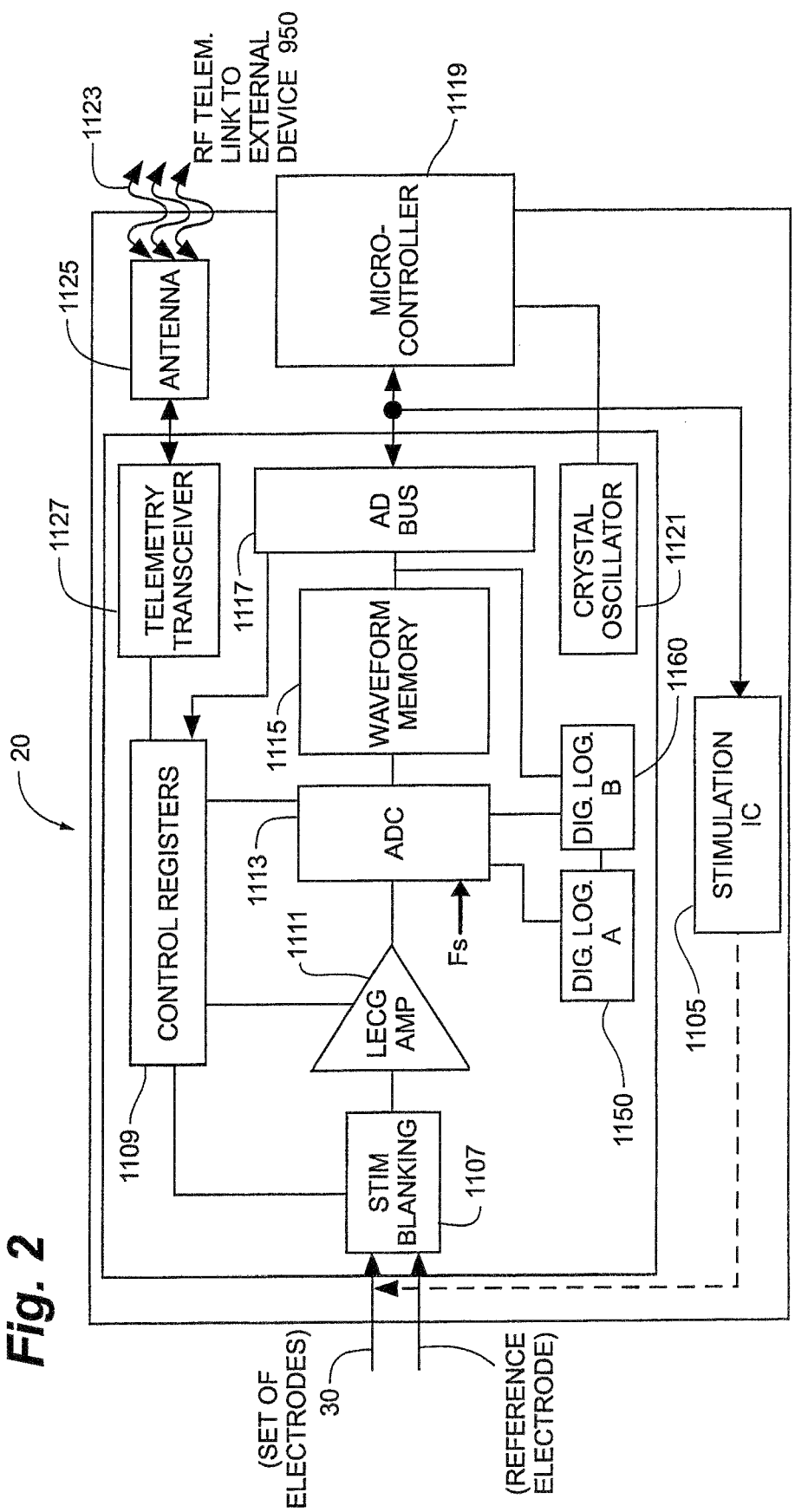
FIG. 2 is a schematic block diagram of an implantable medical device (IMD) for treatment of a nervous system disorder in accordance with embodiments of the invention.

FIG. 2 is a schematic block diagram of an IMD 20. The IMD 20 is implanted in conjunction with a set of electrodes 30. The IMD 20 communicates with an external device, such as programmer 23 (FIG. 1), through a telemetry transceiver 1127, an antenna 1125, and a telemetry link 1123. The external device may collect data from the IMD 20 by placing antenna 24 on the patient's body 12 over the IMD 20 to thereby communicate with antenna 1125 of the IMD 20.

IMD 20 may contain an operating system that may employ a microcomputer or a digital state machine for sensing and analyzing physiological signals in accordance with a programmed operating mode. The IMD 20 may also contain sense amplifiers for detecting signals, and output circuits for delivering electrical stimulation therapy, for example, to certain parts of the brain B. The operating system may include a storage device for storing sensed physiological signals, including those associated with neurological activity. The storage device may also be used for storing operating parameters and other operating history data.

Each electrode of the set of electrodes 30 may be adapted to either receive a physiological signal, such as a neurological signal, or to stimulate surrounding tissue, or to perform both functions. Stimulation of any of the electrodes contained in the electrode set 1101 is generated by a stimulation IC 1105, as instructed by a microprocessor 1119. When stimulation is generated through an electrode, the electrode may be blanked by a blanking circuit 1107 so that a physiological signal is not received by channel electronics (e.g., amplifier 1111). When microprocessor 1119 determines that a channel is able to receive a physiological signal, an analog to digital converter (ADC) 1113 samples the physiological signal at a desired rate (e.g., 250 times per second). Digital logic circuitry, indicated in FIG. 2 by digital logic 1150 and 1160, may be employed to receive the digitized physiological signal from ADC 113. The digitized physiological signal may be stored in a waveform memory 1115 so that the neurological data may be retrieved from the IMD 20 when instructed, or may be processed by microprocessor 1119 to generate any required stimulation signal. In some embodiments, digital logic 1150, 1160 may employ a data compression step, such as applying the new turning point (NTP) algorithm or other suitable algorithms or filters, to thereby reduce memory constraints that may be imposed on an IMD due to issues of size, power consumption, and cost, for example.

Patients with neurological movement disorders, such as Parkinson's Disease, may exhibit abnormal EEG signals indicative of their disease state or condition. The abnormal signals may have characteristics that can serve as identifiers or "biomarkers" of certain neurological disorders. Embodiments of the invention include methods and devices that can monitor such biomarkers in a given patient, and may further provide the ability to treat such a patient (e.g., via electrical stimulation and/or drug therapy). Certain embodiments may include the ability to measure and use a biomarker as an indication of therapy effectiveness, thereby providing a form of closed-loop therapy.

Recorded signals within the basal ganglia (BG) circuit of patients with Parkinson's Disease (PD), for example, may provide a disease state biomarker for PD. When patients are in their "OFF" treatment state, oscillations of local field potential (LFP) signals within the subthalamic nucleus (STN), for example, tend to be dominant within the "antikinetic" beta range (~7-35 Hz) of frequency bands, as shown at 202 in FIG. 3. (There may also be some oscillations in the frequency band of ~2-6 Hz that correlate with tremor.) In the "ON" treatment state, (e.g., with dopamine medication treatment), the pattern of oscillations are greatly reduced in the beta range, and the pattern of oscillations within the "prokinetic" gamma range (greater than about 50 Hz) are enhanced, as shown at 204. The gamma range may encompass frequencies from about 50 Hz to around 1000 Hz, and is also frequently considered to include frequencies above about 60 Hz. The frequency and amplitude of specific peaks within these bands are likely to be patient-specific and may vary between the two hemispheres of the brain in a given patient, for example. Thus, a parameter (e.g., a biomarker) may be defined from measured LPF (or similar) signals and monitored to serve as an overall disease state signal (e.g., as an assessment of a neurological movement disorder). The biomarker may be used to serve as an indicator of therapy effectiveness in a device or system where disruption of antikinetic bands (e.g., beta range) and/or enhancement of prokinetic bands (e.g., via deep brain stimulation (DBS) therapy) may improve related disease symptoms. The biomarker may further be used to provide feedback (e.g., closed-loop feedback) to control the therapy delivery. In some embodiments, the information provided by such a biomarker may provide for the delivery of hemisphere-specific stimulation, which may enhance the ability to provide individualized therapy.

Certain embodiments of the invention include an implantable medical device and/or lead system adapted to electrically stimulate targets in the brain to reduce pathological oscillations that underlay a particular disorder. The device may incorporate open-loop and/or closed-loop feedback, and may be used to treat diseases in which pathological signals or patterns can be detected within the nervous system including movement disorders, epilepsy, and psychiatric and behavioral disorders. Certain embodiments may include independently controlled electrodes (e.g., capable of recording/stimulating) connected to a processor that can store and/or analyze the signal. In an embodiment employing closed-loop feedback, for example, a device may monitor the signal activity, detect any pathological signal(s), process the input, and provide feedback to the controller, which may deliver stimulation therapy to relevant brain circuits as needed to remove any deleterious activity. Stimulation may be provided in a continuous or intermittent manner, as single pulses or bursts of pulses of varying (or random) waveform shapes, amplitudes, pulse widths, and frequencies, for example. The therapy could also be tuned on a patient-specific basis and can be programmed to detect the patterns of a particular patient's neural activity. The stimulation output could also be designed to mimic physiological signals, which could be used to effectively "cancel" certain signals (e.g., pathological signals) using signal processing techniques such as destructive interference and/or noise cancellation, for example.

Figure 4:
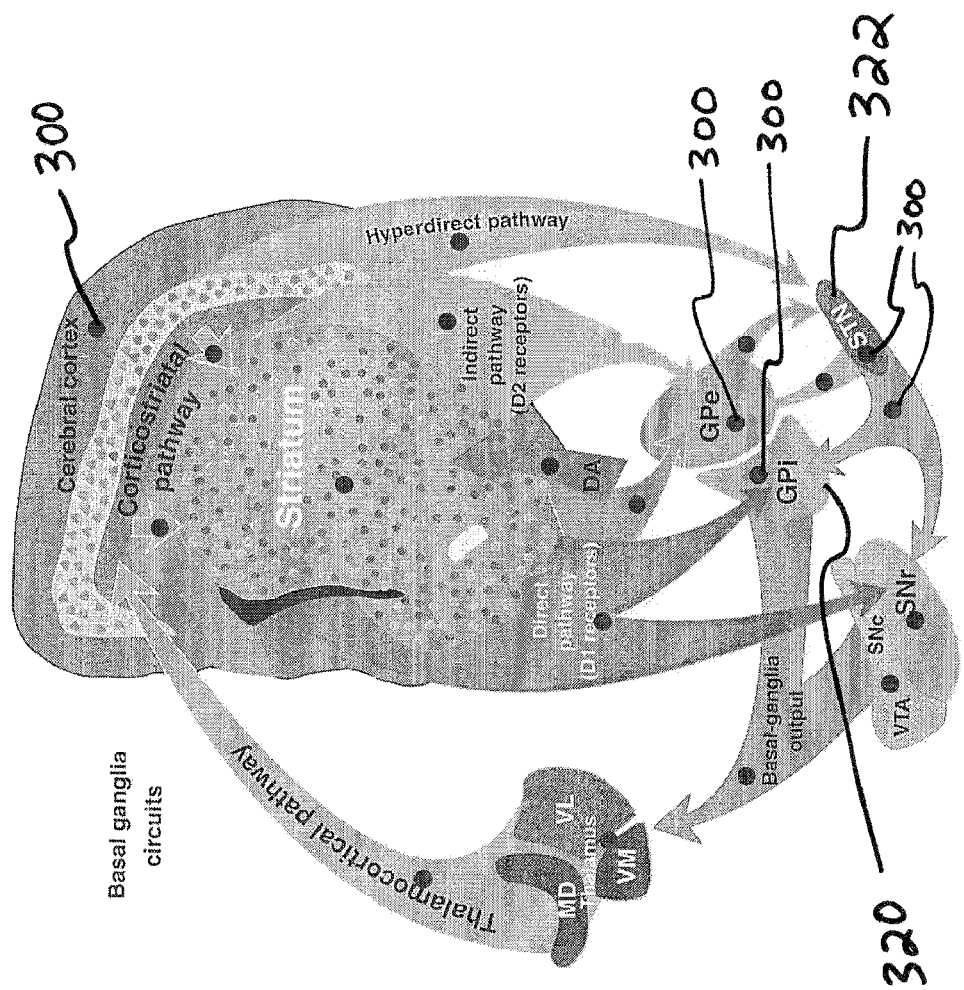
FIG. 4 is a diagram of basal ganglia circuits in a brain, showing potential sensing and stimulation sites for the treatment of neurological movement disorders according to an embodiment of the invention.

FIG. 4 identifies locations 300 that represent possible sensing and/or stimulation sites to disrupt underlying disease oscillations in the basal ganglia (BG). Any nucleus or inter nuclear pathway within the BG circuit could potentially serve as a therapeutic site. In certain embodiments, therapeutic sites may include the globus pallidus internus (GPi) 320, the subthalamic nucleus (STN) 322, and interconnecting pathways. Certain embodiments may provide sensing capabilities at the same site(s) as stimulation, or at any indicated site in the BG on the same or opposite hemisphere. Sensing and stimulation may be conducted simultaneously, or may be alternated, or may be performed independently according to various embodiments. There may be multiple sensing and multiple stimulation sites.

A device according to an embodiment of the invention may determine the presence of specific pathological oscillations and may trigger therapy in response thereto. Contacts and/or electrodes may be used to record and monitor the brain signals, and internal circuitry may decide on the appropriate stimulation (e.g., amount, location, etc.) to alleviate such pathological oscillations (which may result in symptomatic improvement). Recording and stimulation can be done at various points in the pathological network as needed to provide effective signal control.

Figure 5:
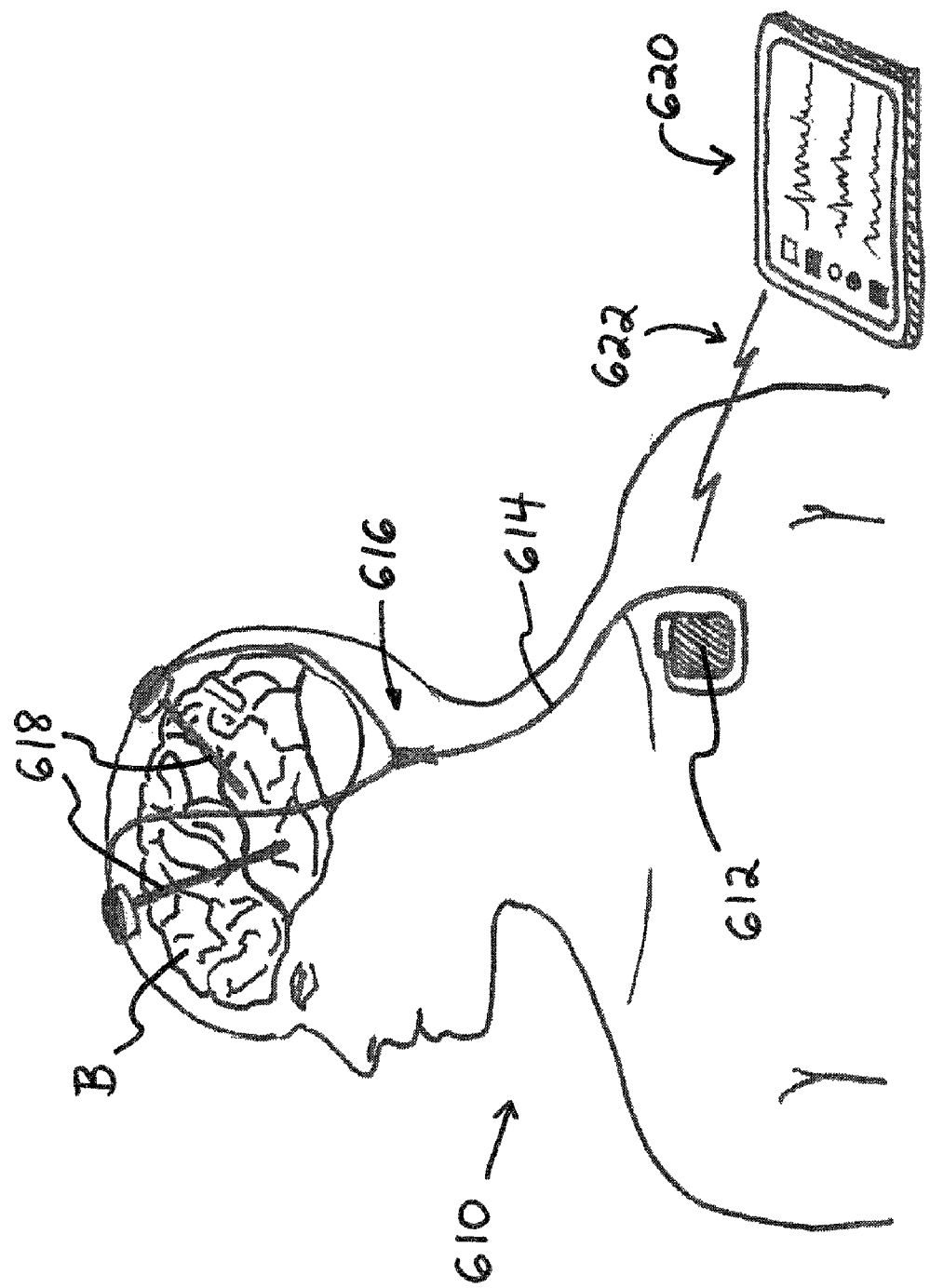
FIG. 5 shows an implantable pectoral device for the treatment of neurological movement disorders according to an embodiment of the invention.

A system in accordance with an embodiment of the invention may include an implantable device, a means for sensing signals from the brain and for delivering therapy to the brain from the implantable device, and an external instrument for programming and operational status. The implantable device can be located subcutaneously, in the torso, as shown in FIG. 5. For example, FIG. 5 shows a patient 610 with an implantable medical device (IMD) 612 implanted subcutaneously. In the particular embodiment shown, IMD 612 is implanted subcutaneously in the left pectoral region of patient 610. Of course, other suitable implant locations may be chosen based on considerations of device size, patient size, physician preference, and/or cosmetic effect, for example, and such locations could include the right pectoral region and abdominal locations. Further, IMD 612 could be implanted using a subcutaneous technique, or comparable locations other than subcutaneous, for example, to address cosmetic concerns (e.g., to minimize the appearance of a "bulge" under the patient's skin).

FIG. 5 shows IMD 612 operably coupled to lead(s) 614. Lead(s) 614 may comprise one or more leads operably coupled to one or more electrodes 618. Electrodes 618 may be adapted to sense signals from the brain and/or may be adapted to sense signals from the brain, for example, in the form of electrical stimulation signals. Lead(s) 614 are adapted to deliver brain signals sensed by electrodes 618 to IMD 612, according to certain embodiments of the invention; lead(s) 614 may be alternately or additionally capable of delivering therapy from IMD 612 to brain B of patient 610 via electrodes 618, according to certain embodiments of the invention. Electrodes 618 may be deep brain electrodes, for example, having a distal end 619 adapted to sense signals from internal regions of the brain. Electrodes 618 may also be surface-type electrodes, which may be located nearer an external part of the brain. Other types of electrodes may also be chosen by one skilled in the art with the benefit of these teachings. In certain embodiments, a number of electrodes 618 may be coupled to lead(s) 614 via an adapter 616 (e.g., a "Y-adapter") to facilitate placement of lead(s) 614 and electrodes 618 inpatient 610.

FIG. 5 also shows an embodiment in which IMD 612 is adapted to communicate with an external programming and/or monitoring device 620, such as programmer 23 described above with respect to FIGS. 1 and 2. Such communications are indicated as telemetry 622, which may include the use of radiofrequency (RF) telemetry signals according to certain embodiments.

Figure 10A:
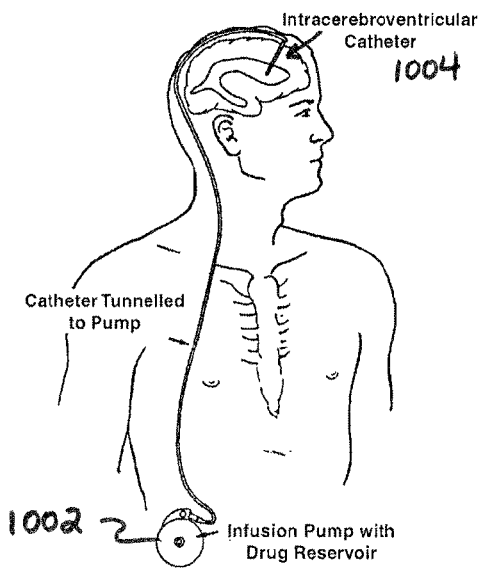
FIGS. 10(A) through 10(D) illustrate exemplary configurations of an implantable infusion pump for the treatment of neurological movement disorders according to embodiments of the invention.
Figure 10B:
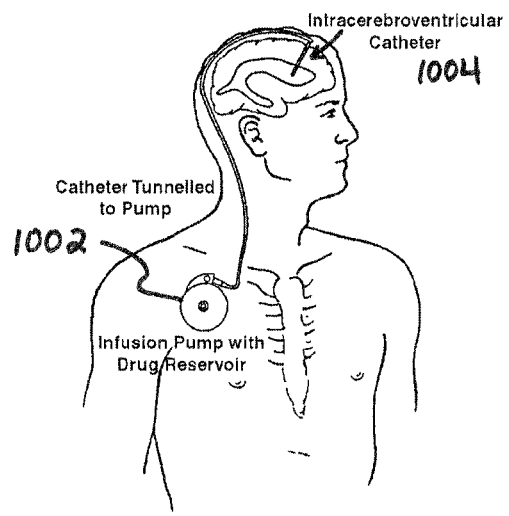
Figure 10C:
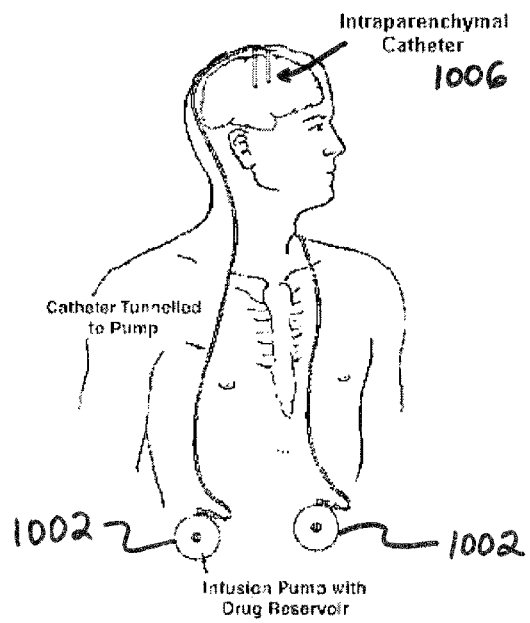
Figure 10D:
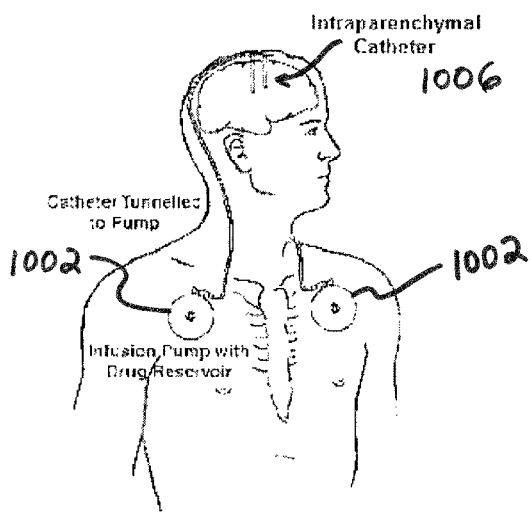

FIGS. 10(A) through 10(D) illustrate exemplary configurations of an infusion pump for the treatment of neurological movement disorders according to embodiments of the invention. FIGS. 10(A) and 10(B), for example, show configurations in which an infusion pump 1002 is adapted to deliver a drug to the brain of a patient via an intracerebroventricular catheter 1004. In FIG. 10(A), the infusion pump 1002 is an implantable device adapted to be implanted in a patient's abdominal area, whereas in FIG. 10(B), the infusion pump 1002 is implanted in a patient's pectoral area. Other suitable implantation locations may be chosen based on physician and/or patient preference, or determined based upon clinical reasons. FIGS. 10(C) and 10(D), for example, show configurations in which an infusion pump 1002 is adapted to deliver a drug to the brain of a patient via one or more intraparenchymal catheters 1006. In FIG. 10(C), the infusion pump 1002 is an implantable device adapted to be implanted in a patient's abdominal area, whereas in FIG. 10(D), the infusion pump 1002 is implanted in a patient's pectoral area. The number and placement of pumps and/or catheters may generally be determined by a physician based on patient and clinical factors. For example, infusion pump 1002 may be an external or wearable device, and/or may be adapted to deliver drug therapy via an infusion insert, for example, located in the skin around a patient's abdomen, or located in any suitable intravenous access point.

Figure 6:
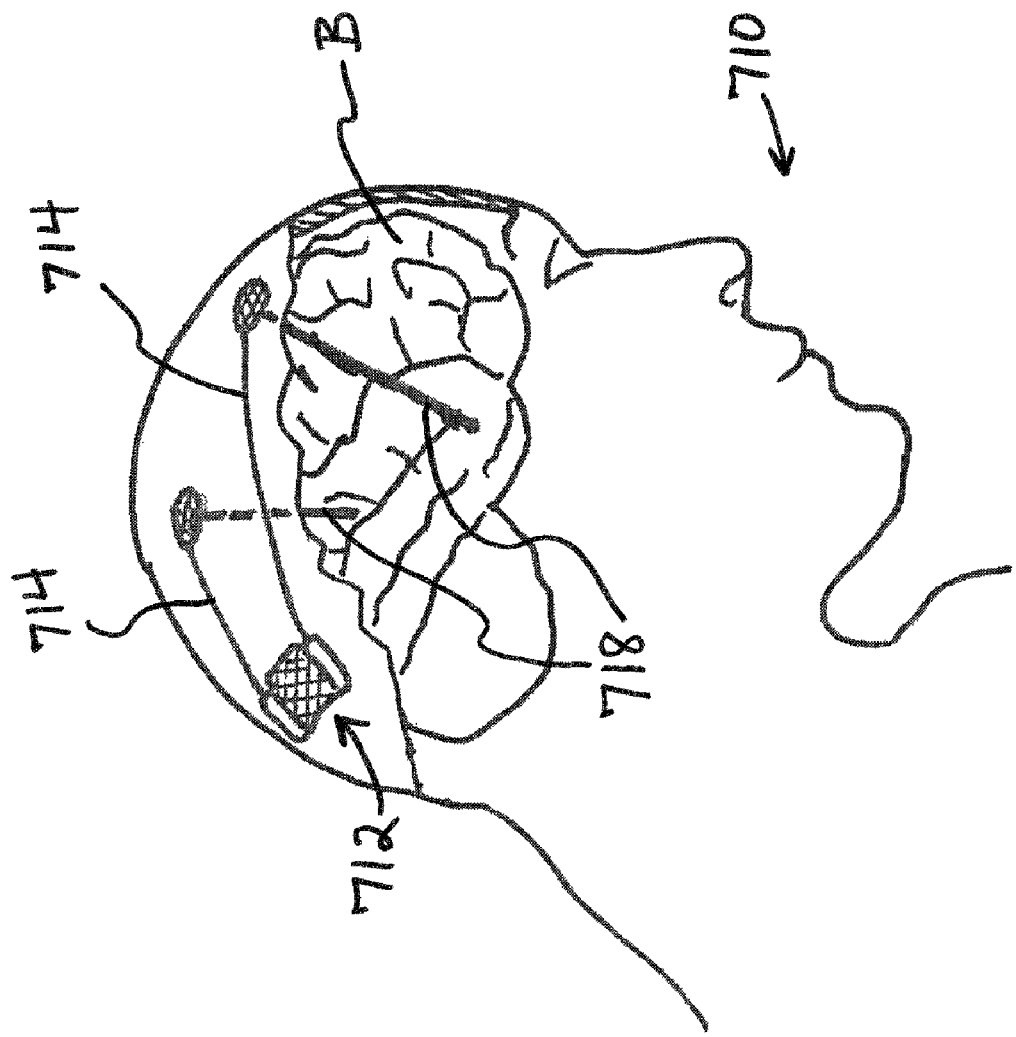
FIG. 6 shows an implantable cranial device for the treatment of neurological movement disorders according to an embodiment of the invention.

In another embodiment, the implantable device may be implanted in the patient's head, as shown in FIG. 6. For example, an IMD 712 may be implanted near brain B of patient 710. Suitable locations for IMD 712 in such an embodiment could be on the surface of the scalp, beneath the skin (e.g., subcutaneously), or intra-cranial locations, as determined by considerations of device size, patient/physician preference, or other factors. IMD 712 may be operably coupled (e.g., via leads 714) to receive brain signals from electrodes 718, and/or to deliver therapy to the brain B of patient 710 via electrodes 718, for example. Therapy delivery may also be provided in the form of drug delivery (e.g., via catheters) to the brain of the patient, or to other therapeutic locations. Electrodes 718 may be similar to those described above with respect to FIG. 5, for example. It is also contemplated that IMD 612 (FIG. 5) and IMD 712 (FIG. 6) could be operably coupled to their respective electrodes 618, 718 via various forms of wireless communication, as are known in the art, rather than via leads 614, 714.

In some embodiments where operable coupling between IMD 612, 712 and electrodes 618, 718 is accomplished via an electrical connection (e.g., via a conductive path comprising one or more wires, such as leads 614, 714), leads 614, 714 may be electrically connected to the implantable device, and may be routed beneath the skin, for example, to be electrically coupled to electrodes 618, 718. Similarly, in embodiments adapted to deliver drug therapy, for example, operable coupling between IMD 612, 712 and outlet ports (not shown) may be via a fluid path comprising one or more catheters operably coupled to IMD 612, 712, which may be routed beneath the skin to therapy delivery sites. The distal end of leads 614, 714 (and/or catheters) may be inserted through a cranial burr-hole and into a specific target of the brain of interest for treatment of the disorder. The distal end of each lead or catheter may terminate with any combination of electrodes and outlet ports. In the case of a patient with Parkinson's Disease (PD), for example, one lead distal end may include one or more electrodes adapted to be located in a region of the brain that may facilitate a reduction in symptoms when therapy (e.g., electrical stimulation) is applied to such location.

A variety of leads and lead types, as are known to those of ordinary skill in the art, may be employed for use with various embodiments of the invention. Stimulation and sensing electrodes referred to herein may assume a variety of different shapes and configurations, such as round electrodes, "windowed" electrodes, spirally wound electrodes, flat electrodes, circular electrodes and so on. Stimulation signals of the present invention may be beamed or directed in certain directions towards desired portions of the brain through various means, such as employing weighted arrays of electrodes, activating certain stimulation electrodes which face in a first direction while turning off other electrodes which face in a direction different from the first direction, and so on. Similarly, arrays of electrodes or multiple electrodes may be employed to more accurately sense and determine the point or region of origin of certain signals generated within the human brain. Leads suitable for use according to embodiments of the invention may include one or more of the following features:

1. Outputs—at least one electrode or catheter outlet port adapted to deliver therapy to the patient. An electrode, for example, may be adapted to deliver electrical stimulation therapy to a portion of a patient's brain. A catheter outlet port, for example, may be adapted to deliver a medicament (e.g., drug) therapy to a patient.

2. Sensing—at least one electrode adapted to sense electrical activity from a patient's brain. In some embodiments of the invention, a lead or lead system may include one or more electrodes which are used both for sensing of electrical activity from a patient's brain, as well as for delivery of electrical stimulation therapy, for example. Other embodiments may employ a lead or lead system that includes the ability to both sense electrical activity from a patient's brain as well as deliver a medicament therapy to the patient.

3. Extension—the ability to add an extension to the wire/catheter/lead/lead system. It may be desirable in some embodiments, for example, to extend an existing lead in order to add to or modify either the sensing or output capabilities of the lead or lead system. For example, it may become desirable to provide sensing and/or therapy at additional locations within a patient's brain, or to enable sensing or therapy to reach locations in the brain that would otherwise be inaccessible.

4. Multiple targets—the ability to provide a furcated wire/catheter/lead/lead system to access multiple targets. It may be desirable in some embodiments, for example, to provide multiple channels of sensing and/or therapy delivery. Multiple channels of sensing, for example, could provide additional information about the nature and location of a neurological event. Multiple channels of therapy delivery may allow for enhanced therapy flexibility, and therefore, potentially more appropriate therapy (e.g., different levels or types of therapy could be selectively delivered or withheld from a plurality of available locations).

An implantable medical device (IMD) according to an embodiment of the invention may contain electronics (e.g., sensing circuitry, memory/storage, logic, and/or processing capabilities) to sense and/or store signals, and may also deliver therapy to the brain through one or more leads (e.g., wires and/or catheters). Research has shown that electrical stimulation and/or medicament application, for example, may have a therapeutic effect on abnormal brain activity. Any combination of these therapies coupled with EEG signal analysis may be performed by an IMD in accordance with embodiments of the invention.

Figure 7:
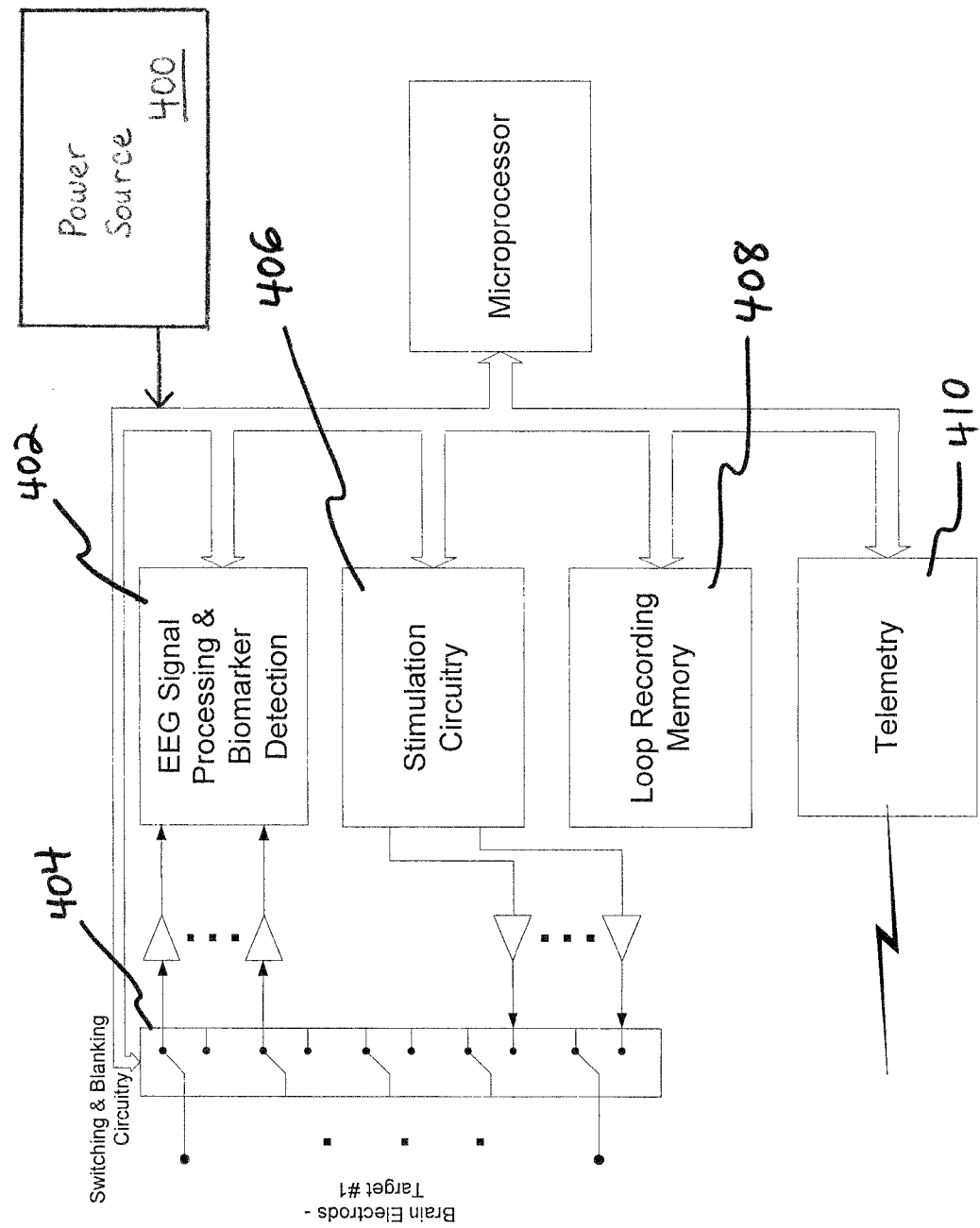
FIG. 7 is a schematic block diagram of an implantable device for treating neurological movement disorders in accordance with an embodiment of the invention.

As shown in FIG. 7, the IMD may include some or all of the following elements:

A Power Source 400 may be either a primary battery or a rechargeable battery, for example, with a recharge coil. A battery provides a source of electrical energy to power the electronics, and to power any electromechanical devices (e.g., valves and pumps) that may be associated with therapy delivery (e.g., medicament delivery and/or electrical stimulation);

Sense circuitry 402 may include EEG amplification, filtering, and biomarker processing circuitry. Filtering, for example, may include bandpass filters for identifying and/or measuring signals in different frequency ranges of interest (e.g., the beta and gamma bands). Bandpass filters may be analog or digital, and may include low-pass and high-pass filters. Biomarker processing may include, for example, circuitry (e.g., microprocessors and/or digital signal processors) for performing computations (e.g., FFT analysis, ratio calculations, etc.);

Control circuitry 404 may include timing, parameter setting, and switching and blanking circuitry. This may include, for example, circuitry that determines the order and speed of input signal acquisition from a number of sources (e.g., multiplexing). During electrical stimulation therapy, for example, blanking circuitry may be employed to avoid false sensing of stimulation signals and/or to protect sensing circuitry. Programmable parameter settings may include, for example, the ability to modify the frequency range or ranges of interest, as well as the calculation of the biomarker itself, Therapy circuitry 406 may include generator circuits for electrical stimulation and/or pump control circuits for drug delivery;

Data recording circuitry 408 may include memory for storing acquired signals and detected events;

Telemetry 410 may provide the ability to communicate with the IMD, for example, providing the ability to program device settings/parameters, to retrieve stored data, and/or to stream received data to an external monitor (e.g., in real-time); and Mechanical packaging of the IMD, which may typically include a biocompatible and hermetically sealed case, connectors, drug pump, and feedthroughs (e.g., electrical and mechanical).

In some embodiments, an implantable device may be adapted to deliver therapy in an open-loop mode (e.g., on a periodic basis), a closed-loop mode (e.g., in response to a biomarker), or a combination of open-loop and closed-loop modes. In the case of certain movement disorders (e.g., Parkinson's), closed-loop therapy may be adjusted (either automatically or manually) in response to measured levels of beta band and/or gamma band activity. Therapy delivery based on measured levels of oscillatory activity in the beta band and/or gamma band may also be beneficial to patients with certain mental health disorders and psychiatric disorders including, but not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (e.g., narcolepsy), obesity, anorexia, and chronic pain disorders.

Figure 3:
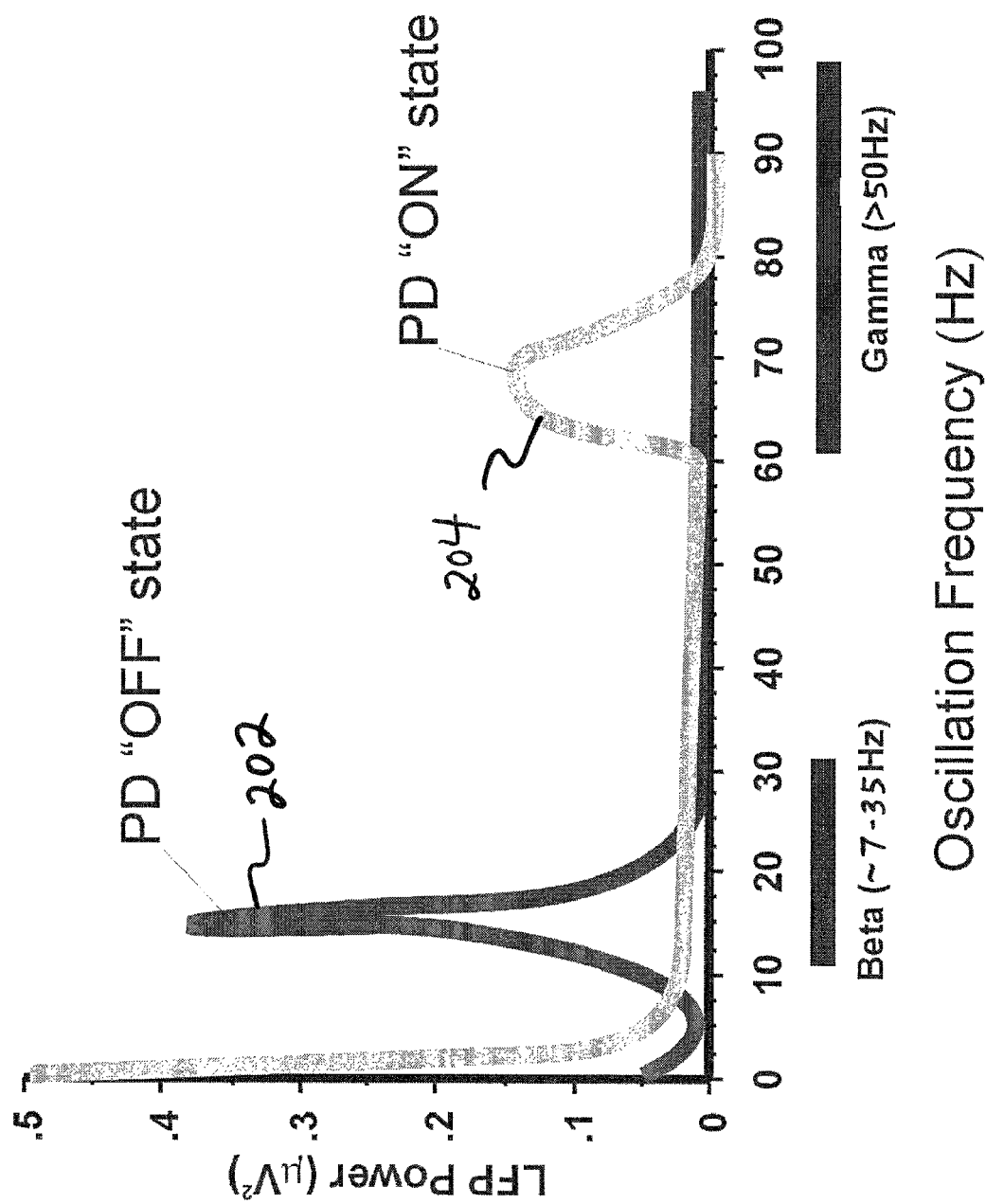
FIG. 3 is a plot of local field potential (LFP) signals that may be used to calculate biomarkers for neurological movement disorders according to an embodiment of the invention.

In one embodiment, closed-loop therapy may be delivered and adjusted by an implantable device, for example, in response to a biomarker determined from the measured levels of oscillatory activity in the beta and gamma frequency bands. One such biomarker may be determined from a ratio of beta and gamma band signal energy, for example. Oscillatory activity (e.g., signal energy) may be quantified in terms of measured local field potential power (e.g., micro-volts$^2$, as shown in FIG. 3), or may be quantified as a relative power (e.g., as a percentage of signal power within a given frequency band to the overall signal power), using fast fourier transform (FFT) techniques, for example. In further embodiments, closed-loop therapy may involve adjusting therapy delivery parameters (e.g., frequency, amplitude, location, drug type, amount, etc.) in order to maintain the measured biomarker within some pre-determined (and/or possibly patient-specific) range of values, for example. In addition to a ratio of signal energies, other biomarkers may be defined that compare signal activity in frequency bands of interest, or which compare signal activity in various locations, for example. For example, average and/or peak signal power levels, Q factor values, and other methods of quantifying the beta and gamma range oscillations, may be used as first and second values from which calculate ratios, difference signals, squared difference values, etc., as would be apparent to one of ordinary skill in the art with the benefit of these teachings.

In some embodiments, an open-loop therapy mode may be provided which allows an operator (e.g., a physician) to review measured levels of beta band and gamma band activity and make adjustments to therapy delivery based thereon. In one embodiment, an operator may retrieve biomarker values determined from the beta and gamma band activity, and use the biomarker values to make adjustments to therapy delivery. Such adjustments may include changes to the programmed therapy delivery settings of an implantable device, for example.

In other embodiments, an implantable medical device or system may provide the ability to store information regarding frequency related oscillatory activity over relatively long periods of time to provide an operator with trending information, for example, to evaluate the effectiveness of therapy over time. The stored information may include one or more biomarkers for evaluating and treating particular movement disorders, such as PD.

Trending information may include, for example, statistical snapshots of data taken over a defined window of time. For example, during a 5 minute window of time, information regarding oscillatory activity may be summarized into one or more statistical measures. [A mean value for the 5 minute window is one example. A median is another. A series of 3 values may be stored for each 5 minute window, comprising a $6^{th}$ percentile value, a $50^{th}$ percentile value, and a $94^{th}$ percentile value, for example.] Such a trending technique may, for example, greatly reduce the memory requirements of an IMD, while retaining useful trending information. The window period and/or the types of statistical measures used could be user-selectable.

Various modes of operation (e.g., open-loop and closed-loop) may provide data storage capabilities (e.g., recording and/or trending of data received), or may allow for the selection of a non-storage mode (e.g., responsive to measured signals and programmed settings, but without data storage). For example, a closed-loop therapy mode, once properly programmed for a particular patient, may have data storage disabled to minimize processing and power demands on a device. Telemetry of data may also be a feature of certain modes of operation, with or without data storage. For example, an open-loop mode may be initiated to allow for testing of programmed settings and/or to determine optimal settings via physician control. Real-time telemetry may be employed during such testing and programming, and data storage associated with such testing may or may not be turned off, depending on physician preference.

Figure 8:
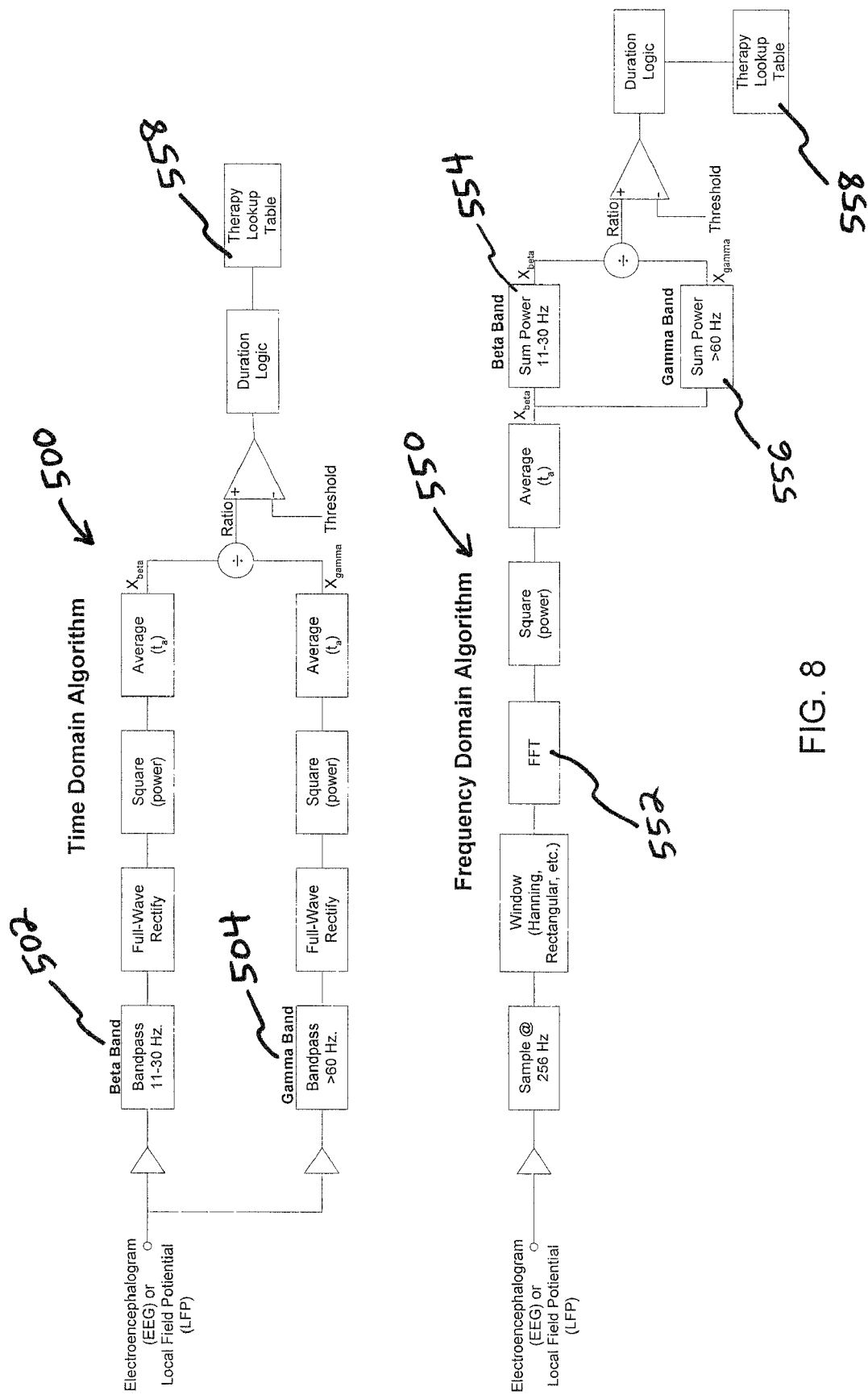
FIG. 8 is a block diagram of a method of determining a biomarker for use in treating neurological movement disorders in accordance with an embodiment of the invention.

Electrode sensors may be used to measure EEG/LFP signals to determine a biomarker. Examples of methods of determining a biomarker in accordance with embodiments of the invention are outlined in the block diagram of FIG. 8. The EEG or LPF signal may be filtered into two discrete frequency bands corresponding to the beta and gamma band biomarkers. This is shown in the time domain algorithm 500 by using bandpass filters (including low-pass and high-pass filters) corresponding to the beta band 502 (~7-35 Hz) and the gamma band 504 (>~50 Hz). This may be accomplished by using analog bandpass filters, or by sampling and using digital bandpass filters, or by sampling and performing time domain-to-frequency domain conversion, or by combinations of these and other methods known to those of ordinary skill in the art. The bandpass filter (or filters) corresponding to the beta band may define other frequency ranges, such as ~11-30 Hz, in some embodiments. Similarly, the bandpass filter (or filters) corresponding to the gamma band may define other frequency ranges, such as ~50-1000 Hz, or ~60-300 Hz, in certain embodiments.

In the frequency domain algorithm 550, a fast fourier transform (FFT) 552 may be applied to the input signal (after appropriate sampling and windowing, for example) to obtain the beta band 554 and gamma band 556 information.

Each of these output signals is processed through an energy averaging algorithm and a comparison of the beta band and gamma band signals is made. In certain embodiments, the comparison may include calculation of the ratio of the beta band signal energy to the gamma band signal energy (or vice versa). The output ratio may then be used to assess the movement disorder, and/or may be compared to a reference value (e.g., a threshold) to assess the movement disorder. The comparison of the ratio value to a predetermined threshold may, for example, provide a signal to adjust therapy delivery accordingly. This may, for example, involve the use of a therapy lookup table 558 according to some embodiments, or may involve a logic function or calculation.

An external instrument may be used for programming the implantable device, viewing device status, and uploading recorded data, for example. It may typically be a computing platform with a graphical user interface that can communicate via telemetry with the implantable device. A communication link may be established that is short range (<1 foot), or long range (>=1 foot). Short-range telemetry may require a telemetry head, which can be tethered or wireless. Software on the computing platform may be adapted to enable management of device parameters.

Figure 9:
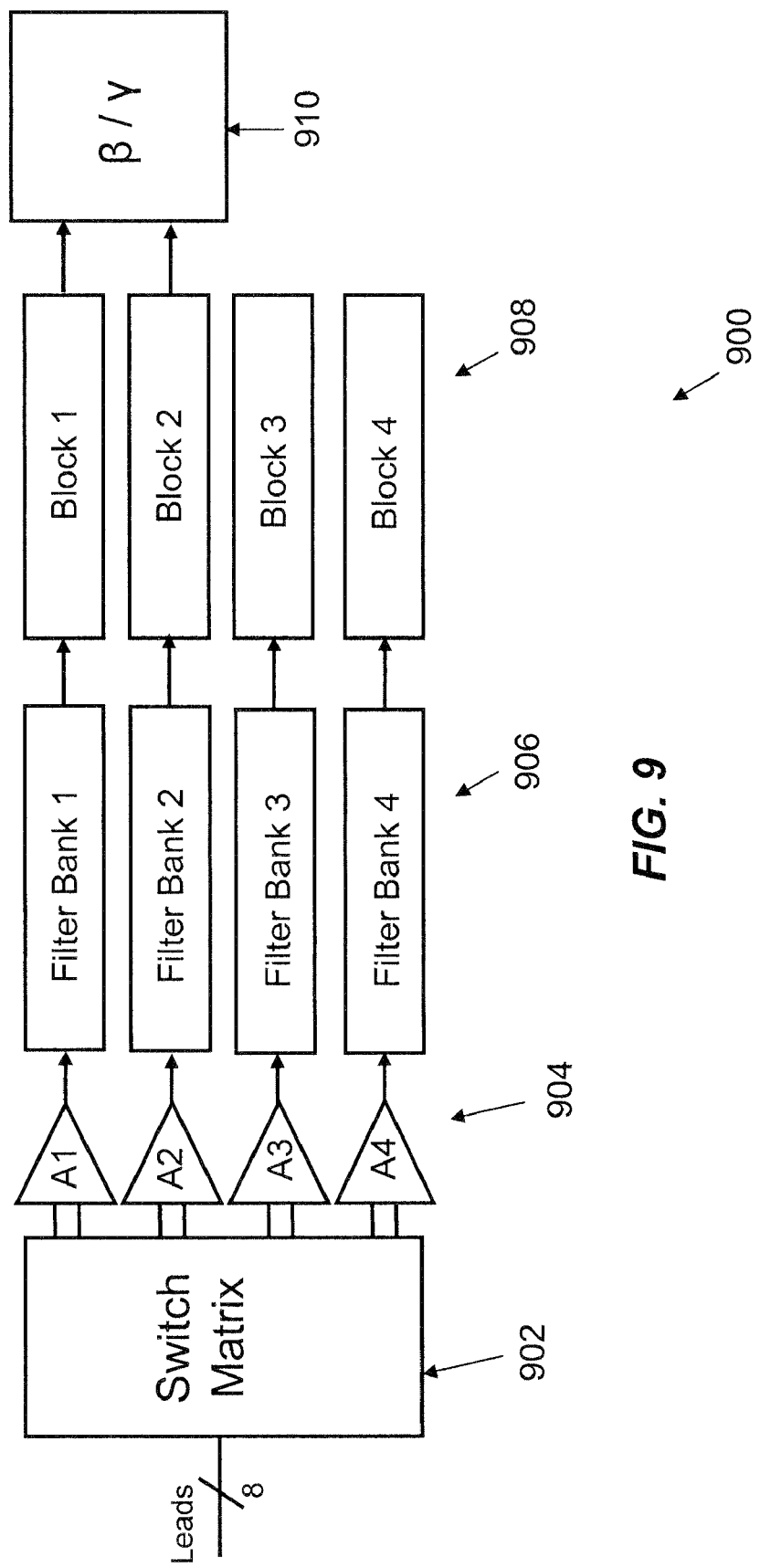
FIG. 9 is a block diagram of a system for treating neurological movement disorders according to certain embodiments of the invention.

FIG. 9 is a block diagram showing a system for treating neurological movement disorders according to certain embodiments of the invention. In FIG. 9, a method of treating neurological movement disorders is incorporated into a system that allows for the selection of input signals. The system also provides for amplification and filtering of the signals before performing a comparison of beta band and gamma band signals.

In FIG. 9, system 900 includes a switch matrix 902 that allows for the selection of a desired combination of input signals (e.g., EEG or ECoG signals acquired from a number of leads adapted to sense brain signals). The switch matrix 902 may be adapted to selectively couple the input signals to one or more amplifiers (e.g., amplifiers A1 through A4 in FIG. 9) in amplifier bank 904. In certain embodiments, two of the amplifiers (e.g., A1 and A2) may receive signals from the same lead combination. The amplified outputs are then coupled to an appropriate filter bank 906. In this example, the outputs of amplifiers A1 and A2 become inputs to Filter Banks 1 and 2, respectively. In certain embodiments, one of the filter banks (e.g., Filter Bank 1) may include (or may be adapted or adjusted to include) filter coefficients corresponding to the beta band, for example. The filter banks 906 may each contain at least one infinite impulse response (IIR) filter. In certain embodiments, a second filter bank (e.g., Filter Bank 2) may include (or may be adapted or adjusted to include) filter coefficients corresponding to the gamma band, for example.

With continued reference to FIG. 9, a bank of processing blocks 908 may be adapted to receive the outputs of the filter banks 906. For example, the outputs of Filter Banks 1 and 2 may be coupled as the inputs to processing blocks 908 (Blocks 1 and 2, respectively, in this example). In certain embodiments of the invention, Blocks 1 and 2 may be adapted to determine an order statistic value (e.g., a median value or other predetermined percentile value) based on a window of data received from the respective Filter Banks 1 and 2. The window of data may correspond, for example, to a predetermined time interval or to a predetermined amount of received data, according to two possible embodiments. Time windows may, for example, correspond to periods of about 1 or 2 seconds in duration, to as long as 30 seconds (or even 30 minutes or more), according to various embodiments. To conserve memory and/or other computing resources, processing blocks 908 (such as Blocks 1 and 2 in this example) may be adapted to employ a multi-stage order statistic (e.g., median) filter to determine an order statistic value. In some embodiments, a two-stage "cascaded" median filter may be employed, for example, in which successive blocks of data are analyzed by a first-stage filter to determine an intermediate median value, then the intermediate values are analyzed by a second-stage filter to determine the cascaded median value. Such multi-stage order statistic filtering may result in a reduction in computing resources, such as memory and processing power.

In certain embodiments of the invention, beta gamma comparator 910 (shown in FIG. 9) receives the outputs of processing blocks 908 and performs a comparison of the beta band signal to the gamma band signal to determine a biomarker according to various embodiments of the invention. In certain embodiments, beta gamma comparator 910 computes a ratio of the beta band signal (e.g., the output of Block 1 in the foregoing example) to the gamma band signal (e.g., the output of Block 2 in the foregoing example). In one particular embodiment, a ratio of the beta band and gamma band signals may be determined using a division approximation technique such as that disclosed in commonly assigned U.S. patent application Ser. No. 10/976,474, the contents of which are incorporated by reference. In some embodiments, the ratio may be calculated with each successive output of the processing blocks 908, or may be calculated less frequently.

Thus, a METHOD AND APPARATUS FOR THE TREATMENT OF MOVEMENT DISORDERS has been provided. While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A system for treating a neurological movement disorder, the system comprising:
    an implantable medical device comprising a housing for a power supply, memory, and electronic circuitry; and
    at least one electrode in communication with the device and adapted to acquire a physiological signal from a brain of a patient, the device being adapted to:
    acquire the physiological signal from the brain of the patient;
    measure a first value from the physiological signal, the first value representative of an amount of oscillatory activity in a first frequency range;
    measure a second value from the physiological signal, the second value representative of an amount of oscillatory activity in a second frequency range;
    calculate a biomarker from the first and second values; and
    use the biomarker to assess the movement disorder, the biomarker being based on a comparison of the first and second values, and the first and second frequency ranges comprising beta and gamma frequency ranges, respectively.

2. The system of claim 1, wherein the device is adapted to calculate the biomarker by at least determining a ratio of the first and second values.

3. The system of claim 1, wherein the device is adapted to deliver treatment to the patient based on the calculated value of the biomarker.

4. The system of claim 3, wherein the device is adapted to deliver treatment to the patient based upon the biomarker exceeding a reference value.

5. The system of claim 3, wherein the treatment comprises at least one of electrical stimulation therapy or drug delivery therapy.

6. The system of claim 3, wherein the device is configured to recalculate the biomarker after delivering the treatment to the patient to provide closed-loop control of the treatment.

7. The system of claim 3, wherein the device is configured to vary the treatment to achieve a biomarker value within a predefined range.

8. The system of claim 1, wherein the first frequency range is about 7 to about 35 Hz, and wherein the second frequency range is greater than about 50 Hz.

9. The system of claim 8, wherein the first frequency range is about 11 to about 30 Hz, and wherein the second frequency range is about 60 to about 300 Hz.

10. The system of claim 1, wherein the device is adapted to compare the biomarker to a reference value to assess the movement disorder.

11. The system of claim 1, wherein the physiological signal comprises at least one of a local field potential signal, an electroencephalogram signal, or an electrocorticogram signal.

12. The system of claim 1, wherein the first and second values are at least partially based on an energy level of the physiological signal within the respective first and second frequency ranges.

13. The system of claim 1, wherein the first and second values are at least partially based on an amplitude of the physiological signal within the respective first and second frequency ranges.

14. The system of claim 1, wherein the first and second values are at least partially based on a frequency of the physiological signal within the respective first and second frequency ranges.

15. The system of claim 1, wherein the device determines at least one of the first or second values representative of an amount of oscillatory activity using an order statistic filter.

16. An implantable medical device (IMD) for treating neurological movement disorders, the device comprising:
one or more electrodes adapted to acquire a physiological signal from a brain of a patient; and
a processing subsystem adapted to determine a first value and a second value from the physiological signal, the first value representative of an amount of oscillatory activity in a first frequency range, the second value representative of an amount of oscillatory activity in a second frequency range, the processing subsystem further adapted to calculate a biomarker as a function of the first and second values, the biomarker providing an assessment of the movement disorder.

17. The IMD of claim 16 further comprising:
a therapy delivery subsystem adapted to deliver therapy to the patient based on the calculated value of the biomarker.

18. The IMD of claim 17, wherein the therapy delivery subsystem is adapted to provide electrical stimulation therapy delivery.

19. The IMD of claim 17, wherein the therapy delivery subsystem is adapted to provide drug therapy delivery.

20. The system of claim 17, wherein the processing subsystem is adapted to control the therapy delivery subsystem to deliver therapy to the patient based on the calculated value of the biomarker exceeding a predetermined threshold.

21. The system of claim 17, wherein the processing subsystem is adapted to re-calculate the biomarker in conjunction with delivery of therapy to provide closed-loop control of the therapy.

22. The system of claim 17, wherein the processing subsystem is configured to vary the therapy delivered by the therapy delivery subsystem to achieve a biomarker value within a predefined range.

23. The IMD of claim 16, wherein the processing subsystem is adapted to control therapy delivery to the patient based on the biomarker.

24. The system of claim 16, wherein the first frequency range is about 7 to about 35 Hz, and wherein the second frequency range is greater than about 50 Hz.

25. The system of claim 24, wherein the first frequency range is about 11 to about 30 Hz, and wherein the second frequency range is about 60 to about 300 Hz.

26. The system of claim 16, wherein the first and second values are at least partially based on an energy level of the physiological signal within the respective first and second frequency ranges.

27. The system of claim 16, wherein the first and second values are at least partially based on an amplitude of the physiological signal within the respective first and second frequency ranges.

28. The system of claim 16, wherein the first and second values are at least partially based on a frequency of the physiological signal within the respective first and second frequency ranges.

29. A method of treating a neurological movement disorder, the method comprising:
acquiring, with a medical device, a physiological signal from a brain of a patient;
measuring a first value from the physiological signal, the first value representative of an amount of oscillatory activity in a first frequency range;
measuring a second value from the physiological signal, the second value representative of an amount of oscillatory activity in a second frequency range;
calculating, with a processor, a biomarker as a function of the first and second values; and
using the biomarker to assess the movement disorder, the biomarker being based on a comparison of the first and second values, and the first and second frequency ranges comprising beta and gamma frequency ranges, respectively.

30. The method of claim 29, wherein the first frequency range is from about 7 to 35 Hz, and wherein the second frequency range is greater than about 50 Hz.

31. The method of claim 30, wherein the first frequency range is from about 11 to 30 Hz, and wherein the second frequency range is between about 60 and 300 Hz.

32. The method of claim 29, wherein calculating the biomarker includes determining a ratio from the first and second values.

33. The method of claim 29, wherein the physiological signal comprises at least one of a local field potential (LFP) signal, an electroencephalogram (EEG) signal, or an electrocorticogram (ECoG) signal acquired by one or more deep brain stimulation (DBS) electrodes located in the brain of the patient.

34. The method of claim 29, wherein the first and second values representative of an amount of oscillatory activity are at least partially based on an energy level of the physiological signal within the respective first and second frequency ranges.

35. The method of claim 29, wherein the first and second values representative of an amount of oscillatory activity are at least partially based on an amplitude of the physiological signal within the respective first and second frequency ranges.

36. The method of claim 29, wherein the first and second values representative of an amount of oscillatory activity are at least partially based on a frequency of the physiological signal within the respective first and second frequency ranges.

37. The method of claim 29, wherein using the biomarker to assess the movement disorder comprises delivering treatment to the patient based on the biomarker.

38. The method of claim 29, wherein delivering treatment to the patient based on the biomarker comprises delivering treatment to the patient based upon the biomarker exceeding a reference value.

39. The method of claim 37, further comprising recalculating the biomarker in conjunction with delivery of treatment to provide closed-loop control of said treatment.

40. The method of claim 39, further comprising varying the treatment to achieve a value of the biomarker within a predefined range.

41. The method of claim 37, wherein delivering treatment to the patient based on the biomarker comprises delivering different treatment in a first region of the brain and a second region of the brain.

42. The method of claim 37, wherein the treatment delivered is varied according to a desired patient outcome.

43. The method of claim 42, wherein the desired patient outcome comprises at least one of improved manual dexterity or a reduction in tremors.

44. The method of claim 29, wherein at least one of the first and second values representative of an amount of oscillatory activity is determined using an order statistic filter.

45. The method of claim 29, further comprising:
measuring a third value from the physiological signal, the third value representative of an amount of oscillatory activity in a third frequency range; and
calculating the biomarker as a function of the first, second, and third values.

46. A non-transitory computer-readable medium programmed with instructions for performing a method of treating a neurological movement disorder, the computer-readable medium comprising instructions that, when executed by a programmable processor, cause the programmable processor to:
acquire a physiological signal from a brain of a patient;
measure a first value from the physiological signal, the first value representative of an amount of oscillatory activity in a first frequency range;
measure a second value from the physiological signal, the second value representative of an amount of oscillatory activity in a second frequency range;
calculate a biomarker from the first and second values; and
use the biomarker to assess the movement disorder, the biomarker being based on a comparison of the first and second values, and the first and second frequency ranges comprising beta and gamma frequency ranges, respectively.

47. The computer-readable medium of claim 46, wherein the instructions cause the programmable processor to calculate the biomarker by at least determining a ratio of the first and second values.

48. The computer-readable medium of claim 46, further comprising instructions that, when executed by the programmable processor, cause the programmable processor to control a medical device to deliver treatment to the patient based on the biomarker.

49. A method of treating a neurological movement disorder, the method comprising:
acquiring, with a medical device, a physiological signal from a brain of a patient;
determining a first value and a second value from the physiological signal, the first value representative of an amount of oscillatory activity in a first frequency range, the second value representative of an amount of oscillatory activity in a second frequency range;
calculating, with a processor, a biomarker as a function of the first value and the second value; and
using the biomarker to assess the movement disorder.

50. The method of claim 49, wherein the first frequency range is from about 0 to 50 Hz.

51. The method of claim 49 wherein the first frequency range is from about 50 to 1000 Hz.

52. The method of claim 49, wherein using the biomarker to assess the movement disorder comprises delivering treatment to the patient based on the biomarker exceeding a predetermined threshold.

53. The method of claim 52, wherein treatment comprises at least one of electrical stimulation therapy or drug delivery therapy.

54. The method of claim 52, further comprising varying the treatment to achieve a value of the biomarker within a predefined range.

* * * * *